(12) United States Patent
Zhadkevich

(10) Patent No.: US 9,655,627 B2
(45) Date of Patent: May 23, 2017

(54) ANTI-EMBOLIC DEVICE AND METHOD

(71) Applicant: Michael Zhadkevich, Inman, SC (US)

(72) Inventor: Michael Zhadkevich, Inman, SC (US)

(*) Notice: Subject to any disclaimer, the term of this patent is extended or adjusted under 35 U.S.C. 154(b) by 687 days.

(21) Appl. No.: 13/859,235

(22) Filed: Apr. 9, 2013

(65) Prior Publication Data

US 2013/0304111 A1  Nov. 14, 2013

Related U.S. Application Data

(60) Provisional application No. 61/646,088, filed on May 11, 2012.

(51) Int. Cl.
*A61B 17/00* (2006.01)
*A61B 17/132* (2006.01)
*A61B 17/135* (2006.01)

(52) U.S. Cl.
CPC ........ *A61B 17/1325* (2013.01); *A61B 17/135* (2013.01)

(58) Field of Classification Search
CPC .............. A61B 17/132; A61B 17/1322; A61B 17/1327; A61B 17/1325; A61B 17/1355; A61B 17/135
USPC .................... 606/201, 202, 203, 204, 204.15
See application file for complete search history.

(56) References Cited

U.S. PATENT DOCUMENTS

| 2,271,927 A | 2/1942 | Saighman |
| 2,571,461 A | 10/1951 | Livingston et al. |
| 2,676,586 A | 4/1954 | Coakwell, Jr. |
| 3,587,584 A | 6/1971 | Bourbon |
| 4,676,232 A | 6/1987 | Olsson et al. |
| 4,686,085 A * | 8/1987 | Osterholm ........... A61K 9/0026 422/45 |
| 4,745,924 A | 5/1988 | Ruff |
| 5,271,409 A | 12/1993 | Millay |
| 5,372,575 A * | 12/1994 | Sebastian ................ A61F 5/012 128/DIG. 20 |
| 5,376,067 A * | 12/1994 | Daneshvar ......... A61B 17/1322 602/13 |
| 5,514,079 A | 5/1996 | Dillon |
| 5,741,295 A | 4/1998 | McEwen |
| 6,063,036 A | 5/2000 | Li |

(Continued)

FOREIGN PATENT DOCUMENTS

| EP | 0109627 A1 | 5/1984 |
| EP | 0 203 310 A2 | 3/1986 |

(Continued)

OTHER PUBLICATIONS

Philipp Kahlert; titled "Cerebral Embolization During Transcatheter Aortic Valve Implantation: A Transcranial Doppler Study"; item title "Journal of the American Heart Association"; copyright Aug. 16, 2012; pp. 1245-1255; No. 126; American Heart Association, Inc.; Dallas, Texas, USA; copy enclosed (16 pages).

(Continued)

*Primary Examiner* — Diane Yabut
*Assistant Examiner* — Martin T Ton
(74) *Attorney, Agent, or Firm* — J. Bennett Mullinax, LLC

(57) ABSTRACT

A device for use in preventing stroke is provided. The device may include an expandable member that expands from a non-expanded configuration to an expanded configuration. The expandable member is located at a neck of a patient. An associated method is provided.

28 Claims, 16 Drawing Sheets

(56) References Cited

U.S. PATENT DOCUMENTS

| | | | |
|---|---|---|---|
| 6,336,901 | B1 | 1/2002 | Itonaga et al. |
| 7,727,254 | B2 | 6/2010 | Pah |
| 7,972,356 | B2 | 7/2011 | Boyle et al. |
| D643,536 | S | 8/2011 | Vivenzio |
| 7,998,104 | B2 | 8/2011 | Chang |
| 8,025,674 | B2 | 9/2011 | Barbut et al. |
| 8,062,324 | B2 | 11/2011 | Shimon et al. |
| 2001/0025643 | A1* | 10/2001 | Foley ............... A61F 2/24 128/898 |
| 2004/0098035 | A1* | 5/2004 | Wada ............ A61B 17/1325 606/201 |
| 2005/0075531 | A1 | 4/2005 | Loeb et al. |
| 2008/0154140 | A1 | 6/2008 | Chang et al. |
| 2008/0262535 | A1 | 10/2008 | Gavriely et al. |
| 2009/0209925 | A1* | 8/2009 | Marinello ............ A61K 31/26 604/308 |
| 2010/0082060 | A1* | 4/2010 | Avitable ............ A61H 9/0078 606/202 |
| 2010/0324589 | A1 | 12/2010 | Carpenter et al. |
| 2011/0028934 | A1* | 2/2011 | Buckman ............ A61B 17/135 604/385.12 |
| 2013/0023909 | A1 | 1/2013 | Duhay |
| 2014/0236221 | A1 | 8/2014 | Zhadkevich |

FOREIGN PATENT DOCUMENTS

| | | |
|---|---|---|
| EP | 0 934 726 A1 | 8/1999 |
| EP | 2662034 A1 | 11/2013 |
| EP | 2796099 A1 | 10/2014 |
| FR | 699 349 | 2/1931 |
| FR | 719 730 A | 2/1932 |
| WO | WO 98/46144 A1 | 10/1998 |
| WO | WO 99/36028 | 7/1999 |

OTHER PUBLICATIONS

Marie-Christine Guilbert, MD; titled "Arterial trauma during central venous catheter insertion: Case series, review and proposed algorithm"; item title "Journal of Vascular Surgery"; copyright 2008; pp. 918-925; vol. 48, No. 4; Canadian Society for Vascular Surgery; Montreal, Quebec, Canada; copy enclosed (8 pages).

Gabor Erdoes, MD; titled "Letter by Erdoes et al Regarding Article, "Cerebral Embolization During Transcatheter Aortic Valve Implantation: A Transcranial Doppler Study""; item title "Journal of the American Heart Association"; copyright 2013; p. 590; No. 127; American Heart Assoication, Inc.; Dallas Texas, USA; copy enclosed (2 pages).

European Patent Office; Extended European Search Report; European Application No. 13167290.9-1654; European Patent Office; pp. 1-10; publisher European Patent Office; Published Munich, Germany; copyright and mailing date Aug. 6, 2013; copy enclosed (10 pages).

European Search Report; Extended European Search Report; European Application No. 14166170.2-1654; European Patent Office; pp. 1-7; publisher European Patent Office; Published Munich, Germany; copyright and mailing date Jul. 28, 2014; copy enclosed (7 pages).

H. Loffler; Stratum corneum adhesive tape stripping: influence of anatomical site, application pressure, duration and removal; British Journal of Dermatology; 2004; pp. 746-752; vol. 151; publisher United States Patent and Trademark Office; Published united Kingdom; copyright 2004 British Association of Dermatologists; copy enclosed (8 pages).

* cited by examiner

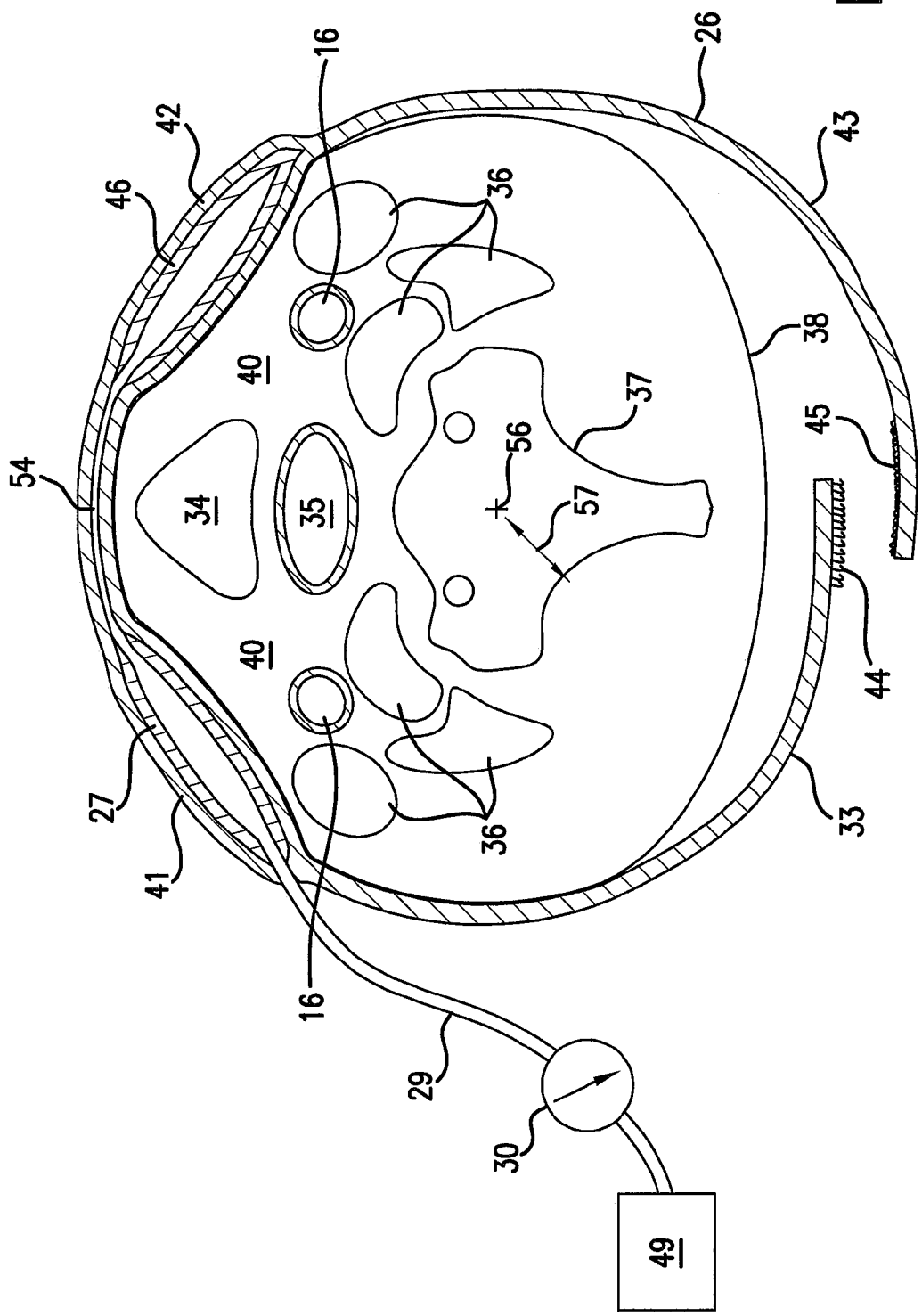

ANTI-EMBOLIC DEVICE AND METHOD

CROSS REFERENCE TO RELATED APPLICATION

This application claims the benefit of U.S. Application Ser. No. 61/646,088 filed on May 11, 2012 and entitled, "anti-embolic neck collar." U.S. Application Ser. No. 61/646,088 is incorporated by reference herein in its entirety for all purposes.

FIELD OF THE INVENTION

The present invention relates to a device and method for preventing cerebral emboli and stroke as a consequence of "emboligenic" interventions on the heart, heart valves, coronary arteries and aorta. More particularly, the present application involves a pressurized compression device that induces temporary noninvasive external extravascular compression and occlusion of carotid arteries at the moment of emboligenic intervention.

BACKGROUND

Intraoperative embolic stroke is one of the most dreadful complications of cardiac, aortic and vascular procedures, diagnosed in 1-22% of patients undergoing cardiovascular surgery. Even more frequently, in up to 70% of cases, patients undergoing heart, valve, coronary artery bypass and aortic surgery experience subclinical embolic events as recorded by transcranial Doppler and MRI. These embolic events lead to cognitive impairment and disability and have a significant impact on patients' recovery.

The main sources of cerebral emboli and stroke in this setting resides in the heart, heart valves, thoracic aorta, and great vessels when these structures are intervened thereon. Even simple cardiac catheterization with an endovascular catheter can induce microtrauma of the atherosclerotic thoracic aorta leading to formation of embolic particles with subsequent embolic brain injury ranging from latent ischemic foci to a massive or even fatal stroke.

Multiple devices are known that attempt to prevent embolization of the carotid arteries during endovascular and cardiac interventions by using different types of filters, deflection devices or endoluminal balloons. These anti-embolic devices, however, have not received wide acceptance in surgery of the heart, heart valves and thoracic aorta due to their complexity and invasive character with the risk of additional trauma to the inner vessel wall resulting in a high risk to benefit ratio. Known devices require insertion of additional hardware into the arterial system or aorta, a procedure that is known by itself to be associated with all classical risks of endovascular intervention, including aortic dissection, bleeding, thrombosis, and carotid cerebral embolization and stroke. One known intra-aortic filter device that is inserted into the ascending portion of the thoracic aorta via an aortic cannula to capture potential embolic material released from the heart and aortic wall during heart surgery was found to be quite difficult to implement and was reported to be associated with major trauma to aortic wall and acute aortic dissection.

Aside from introducing hardware into the patient and causing the aforementioned problems, intravascular filters are not able to capture embolus smaller than the pore size of the available devices (currently 60-140 μm) resulting in cerebral microembolization. Furthermore, the placement of the filter by itself may produce cerebral emboli. For example, the mere passing of a guide wire into a carotid artery generates approximately 40,000 microemboli, with a significant percentage of small, less than 60 μm, particles that are not retained by standard filters. Therefore, in spite of multiple innovations in the field of anti-embolic devices, the problem of cerebral emboli and stroke during cardiovascular surgery is far from being resolved. As such, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 8A is a cross-sectional view of a neck of a patient and a device attached thereto in an unactuated state.

Figure 1:
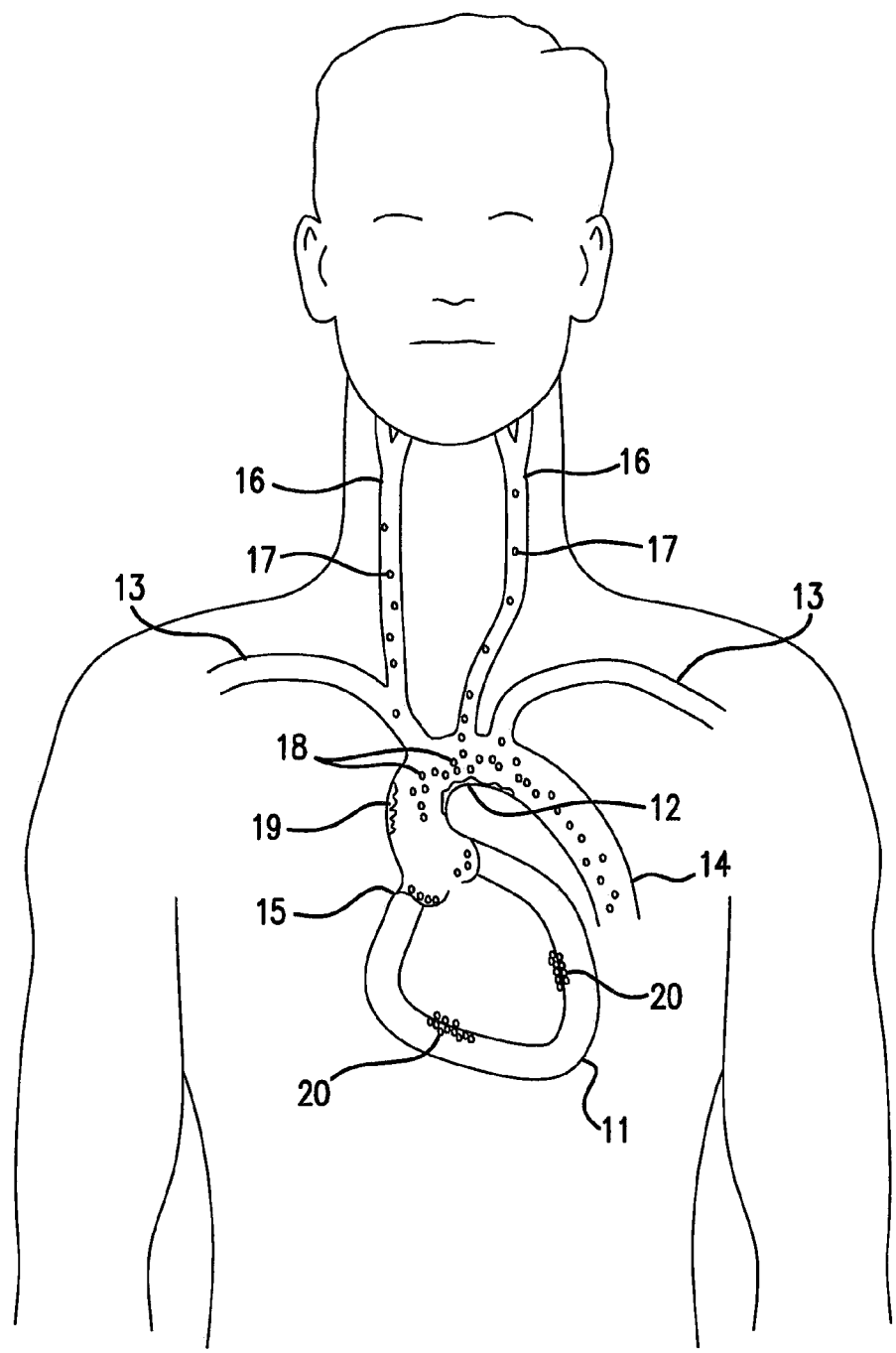
FIG. 1 is a front view of a patient with emboli in the heart and ascending thoracic aorta with subsequent propagation of emboli into both carotid arteries with the source of emboli being diseased aorta, aortic valve and the heart.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an apparatus and method of preventing stroke by diverting emboli from cerebral circulation. A device 26 is placed around the neck of a patient that is non-invasive and can include a longitudinal carotid expandable member 27 and/or a transverse carotid expandable member 32. The members 27 and 32 can be expanded from an unactuated state to an actuated state in which the members 27 and 32 create an area of compression 23 at the carotid arteries 16 to prevent blood flow therethrough into the cerebral circulation. Emboli 17, 18 that are formed in the patient secondary to emboligenic intervention are diverted into a descending aorta 14 and other vascular structures.

With reference to FIG. 1, a front view of a patient is shown in which emboli 18 are transferred from the aortic arch 12 into the carotid arteries 16. The emboli 17 that are present in the carotid arteries 16 can then be transferred into the cerebral circulation causing stroke of the patient. The emboli 18 may be fragments of atherosclerotic plaque 19 of the aorta 12 that become dislodged during manipulation of the ascending thoracic aorta 12. Also shown in FIG. 1 is calcification of the aortic valve 15 and intracardiac emboli 20 of the heart 11 that can also be the origin of emboli 17 eventually present in the carotid artery 16. The intracardiac emboli 20 may include air, gas, thrombi and atherosclerotic materials. Although all of the various emboli in the heart 11, aortic arch 12 and aortic valve 15 need not be present in all instances, they are all shown in FIG. 1 for sake of example. Trauma to the heart 11, aortic valve 15 and aortic structures during placement and removal of items such as an aortic clamps, balloon valvuloplasty and electrophysiological instruments, along with manipulations such coronary artery bypass grafting, aortic and mitral valve replacement, catheter ablation, endovascular grafting of the aorta 12, percutaneous implantation of the aortic or mitral valves, endovascular manipulations on the aorta 12, aortic branches and the heart 11 may give rise to the presence of emboli 17 in the carotid arteries 16. Critical moments of the aforementioned procedures (for example during the aortic cross clamp manipulation, aortic valvuloplasty or valve implantation, coronary interventions, and endovascular procedures on the aorta) may cause emboli 17 to form and cause stroke and are referred to as "emboligenic" events.

Figure 2A:
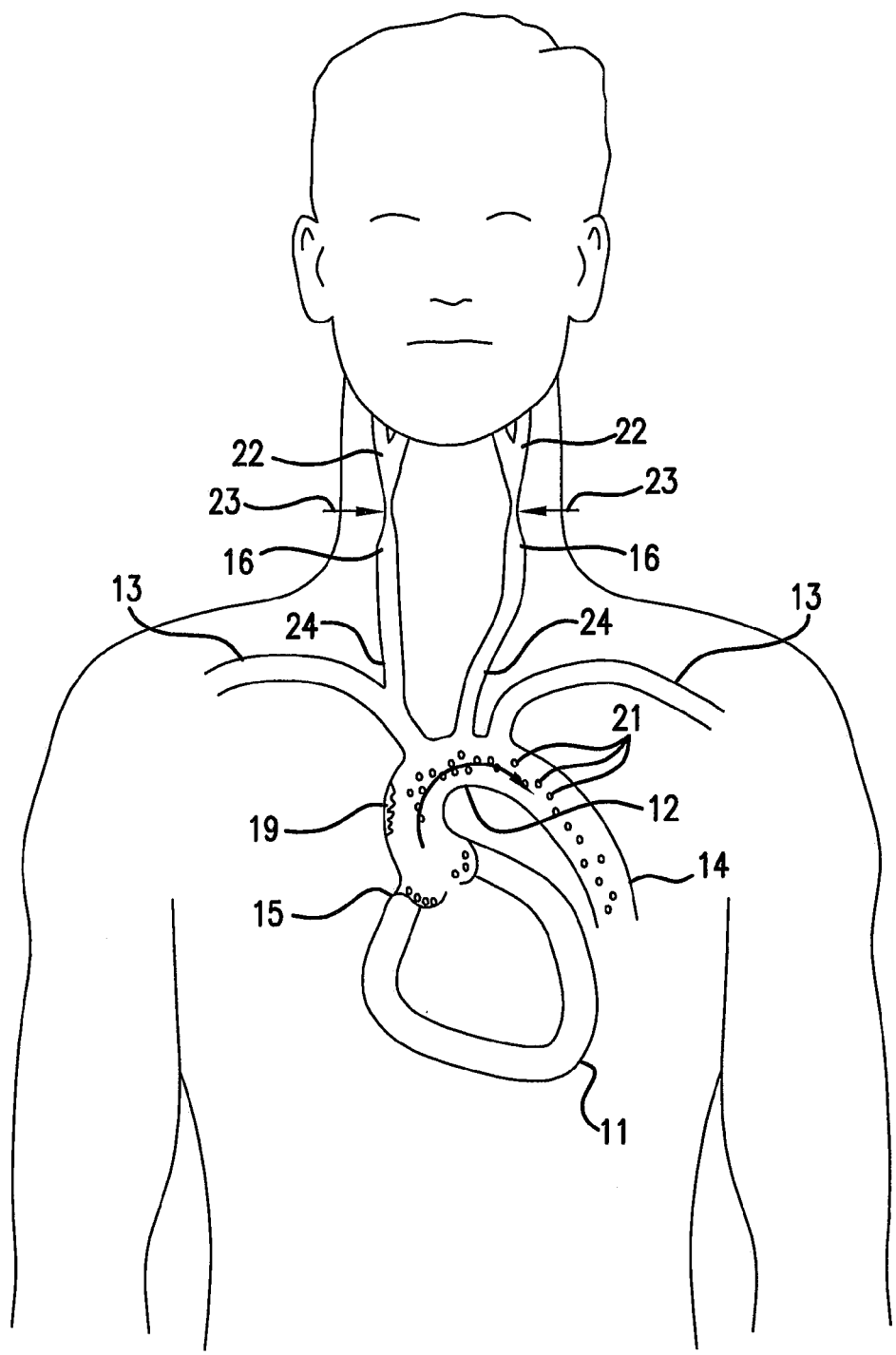
FIG. 2A is a front view of a patient with external compression of both carotid arteries that leads to temporary interruption of the carotid arterial flow.
Figure 2B:
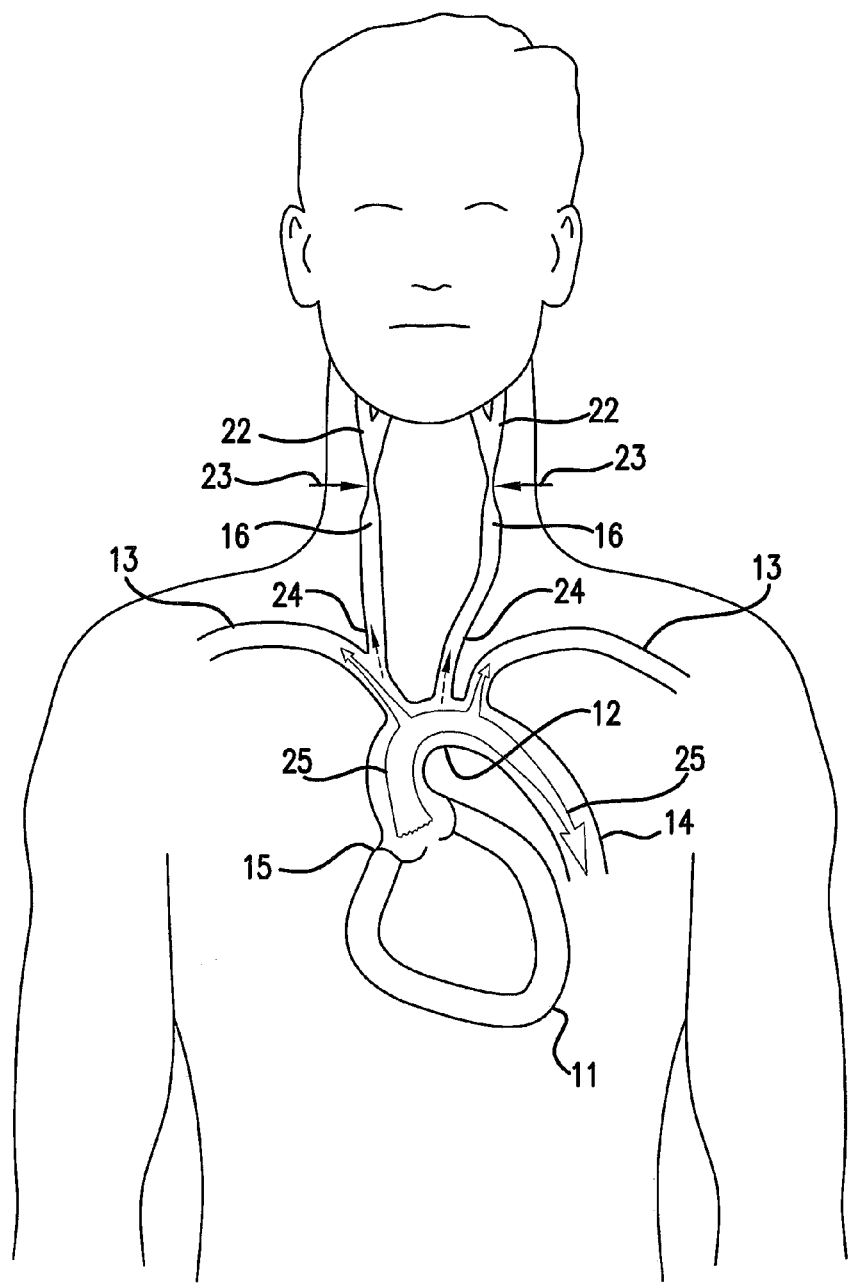
FIG. 2B is a front view of a patient with external compression that results in divergence of flow that carries emboli to the descending aorta and other vascular structures.

FIGS. 2A and 2B show the disclosed method of diverging emboli 18 from cerebral circulation by exerting external compression to form areas of compression 23 at the carotid arteries 16 to lead to temporary interruption of carotid flow. The distal carotid arteries 22 are present downstream from the areas of compression 23, and the proximal carotid arteries are the portions of carotid arteries 16 upstream from the areas of compression 23. Upon creation of the areas of compression 23, a relative pressure gradient and a "no-flow" condition is produced in the proximal carotid arteries 24 that prevents emboli 18 from entering the cerebral circulation. The proximal carotid arteries 24 are areas of the carotid arteries 16 upstream from the areas of compression 23 that have interrupted blood flow due to the compression. Potential carotid emboli 17 are diverted into the descending aorta 14 and are illustrated as emboli 21. The arrow 25 shows preferential direction of the blood flow that carries potential cerebral emboli 17 into the descending aorta 14 when the areas of compression 23 are created.

FIGS. 3A-3D disclose an exemplary embodiment of a device 26 that can be used to create the areas of compression 23 previously described to deflect emboli 17 from the carotid arteries 16 to prevent emboli in the cerebral circulation. The device 26 can be positioned on the neck of the patient so that a pair of straps 33 and 43 extend around to the back of the neck of the patient and are secured to one another via hooks 44 and loops 45 that form a hook and loop type arrangement. However, it is to be understood that other mechanisms of securing the straps 33 and 43 to one another are possible and that the disclosed arrangement is only one exemplary embodiment. Securement of the hooks 44 and loops 45 causes the device 26 to be retained onto the neck of the patient. This retention may be loose so that the device 26 has some room to give on the neck, or the retention may be of a tightness that firmly secures the device 26 onto the neck and prevents same from moving or twisting. The device 26 may be a neck collar in accordance with various exemplary embodiments. In other arrangements the device 26 may be a strap that lays on the front of the neck of the patient, or may be made of multiple components that are not directly attached to one another but are positioned proximate to the neck of the patient. The device 26 may include two semi-oval halves that may be positioned around the neck of the patient in accordance with one exemplary embodiment. The device 26 need not be circular in shape. Even if the device 26 is not circular in shape it may still have a central axis 56 as the central axis 56 can be located at the center of the neck of the patient and thus may still be a central axis 56 of the device 26.

Figure 3A:
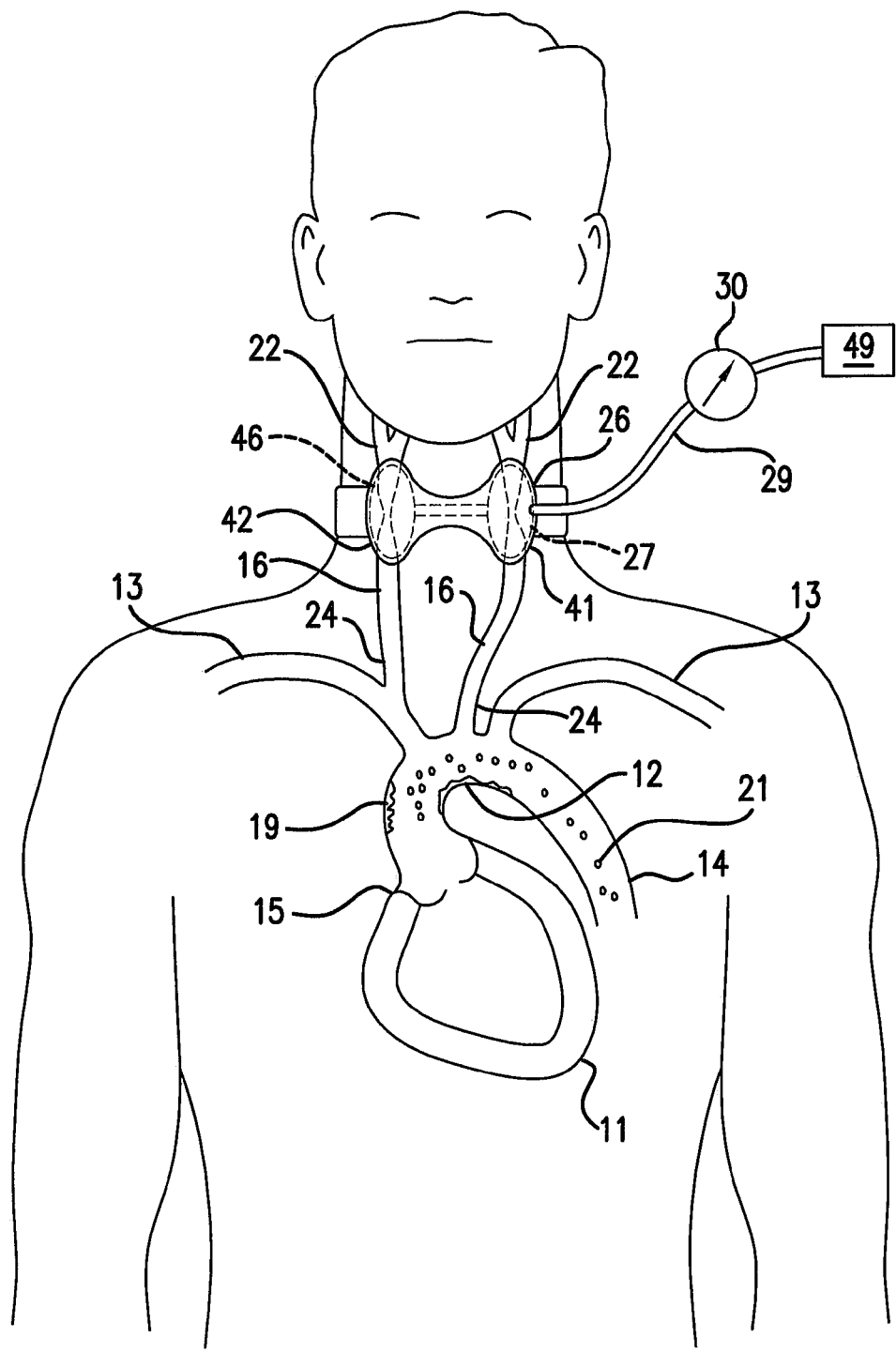
FIG. 3A is a front view of a patient with a device that is actuated in order to achieve external compression.
Figure 3B:
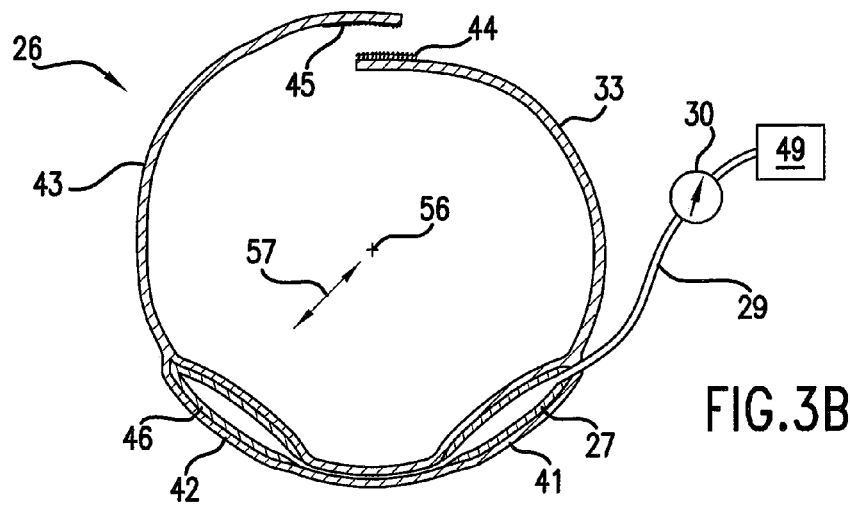
FIG. 3B is a cross-sectional view of the device of FIG. 3A in an unactuated state.

With reference in particular to FIG. 3B, a pair of insertion pockets 41 and 42 are present on the device 26 and may be sealed at their tops and bottoms with respect to the vertical direction 55. As used herein, the vertical direction 55 may be the direction of the device 26 that is parallel to the direction of extension of the central axis 56. Strap 33 may extend from the first insertion pocket 41, and strap 43 may extend from the second insertion pocket 42. The first insertion pocket 41 forms a cavity into which a first longitudinal carotid expandable member 27 is located. Member 27 is shown in a deflated or unactuated state in FIG. 3B and may be made of a flexible material that can be stretched or otherwise deformed. The material making up member 27 can be nonporous such that member 27 is capable of being filled with gas or liquid that enables the member 27 to expand and at the same time hold the gas or liquid therein. The pocket 41 may be made of a material that is different than the material making up member 27.

The second insertion pocket 42 forms a cavity into which the second longitudinal carotid expandable member 46 is retained. Member 46 may be configured in a manner similar to member 27 and a repeat of this information is not necessary. Member 46 may be completely sealed except for an opening that leads into connecting tube 54. Member 46 is in an unactuated state in FIG. 3B.

Figure 3C:
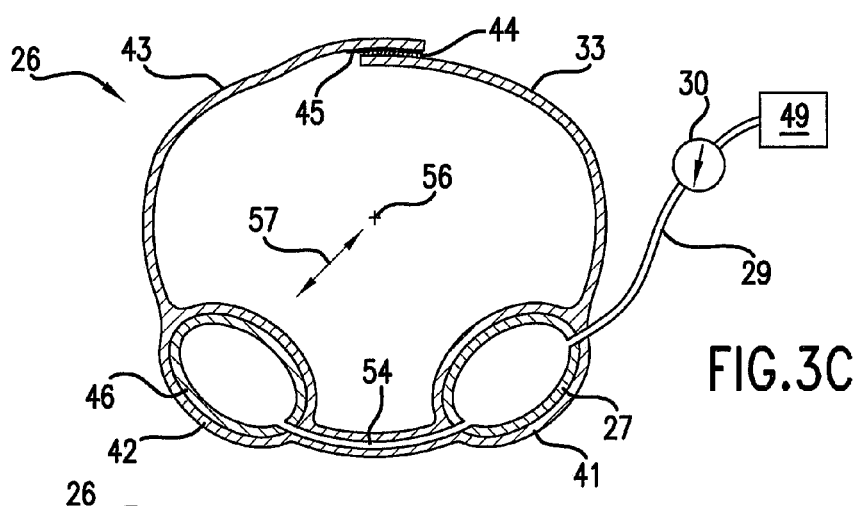
FIG. 3C is a cross-sectional view of the device of FIG. 3A in an actuated state.
Figure 3D:
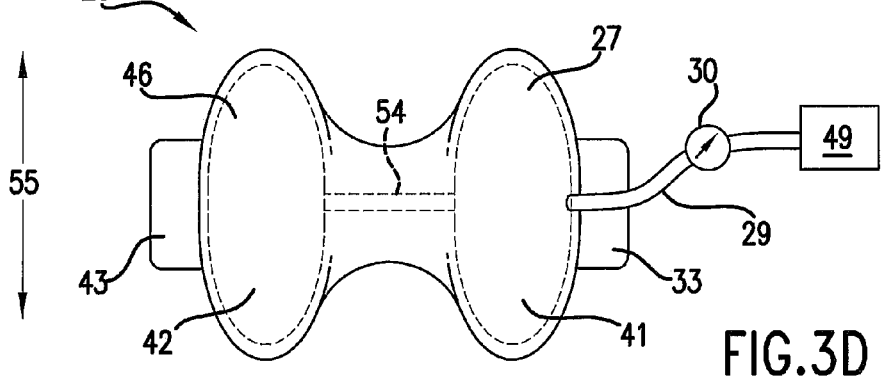
FIG. 3D is a front view of the device of FIG. 3A in an actuated state.
Figure 4A:
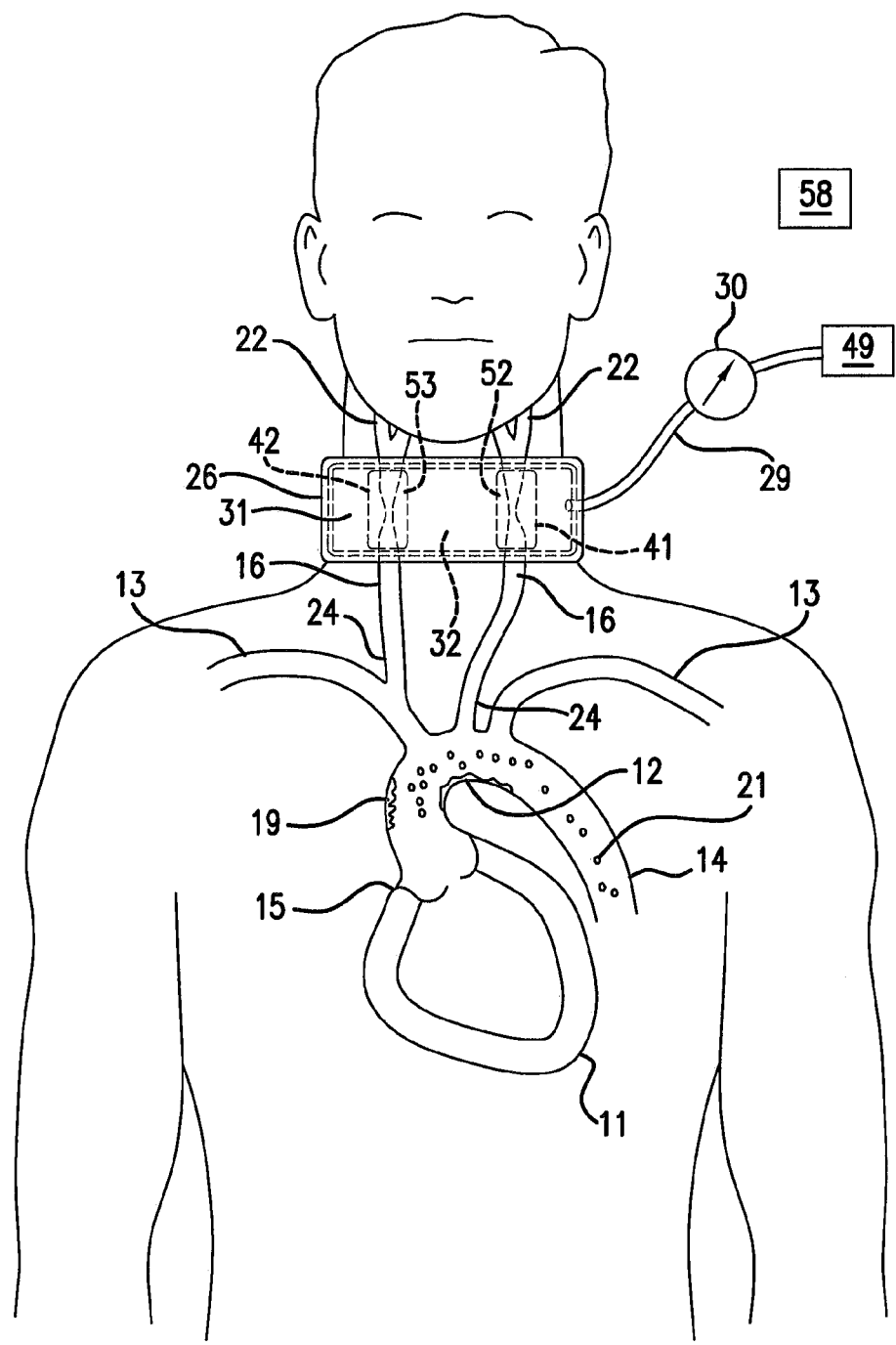
FIG. 4A is a front view of a patient with a device that features first and second compression members in accordance with another exemplary embodiment.
Figure 4B:
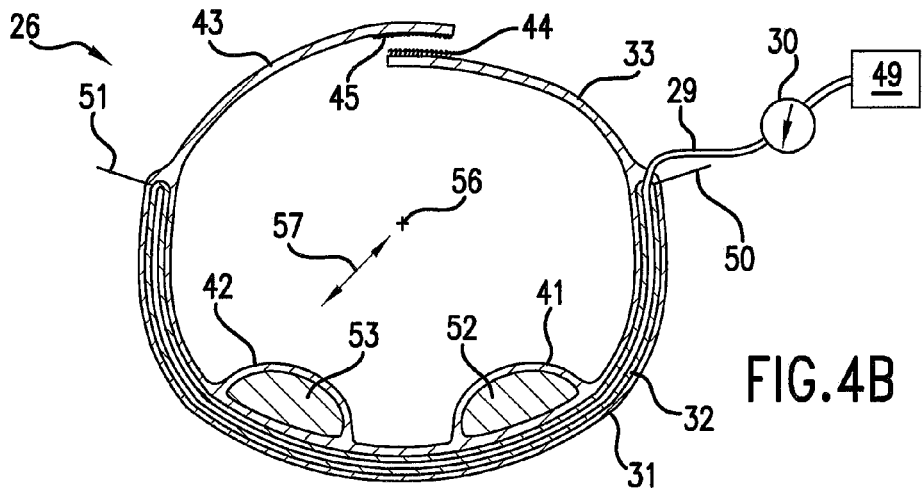
FIG. 4B is a cross-sectional view of the device of FIG. 4A in an unactuated state.
Figure 4C:
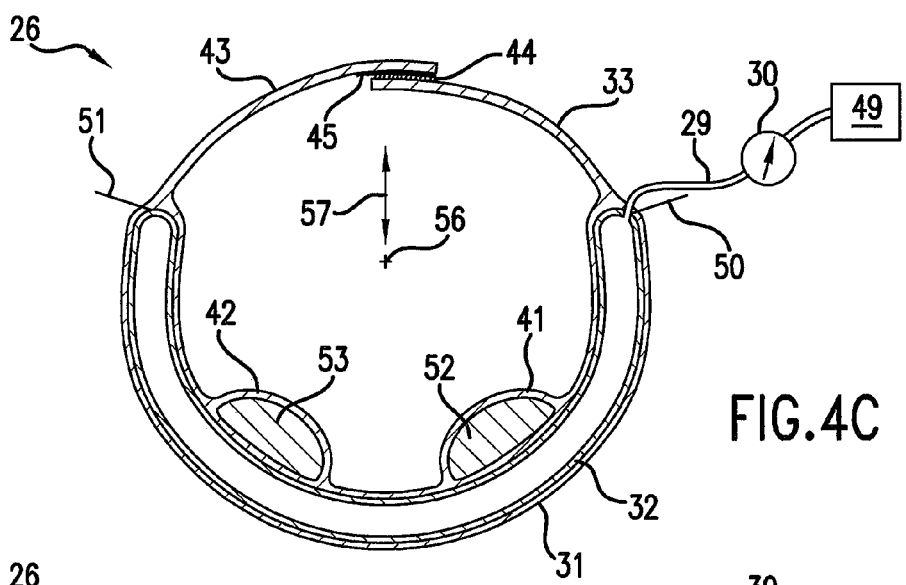
FIG. 4C is a cross-sectional view of the device of FIG. 4A in an actuated state.
Figure 4D:
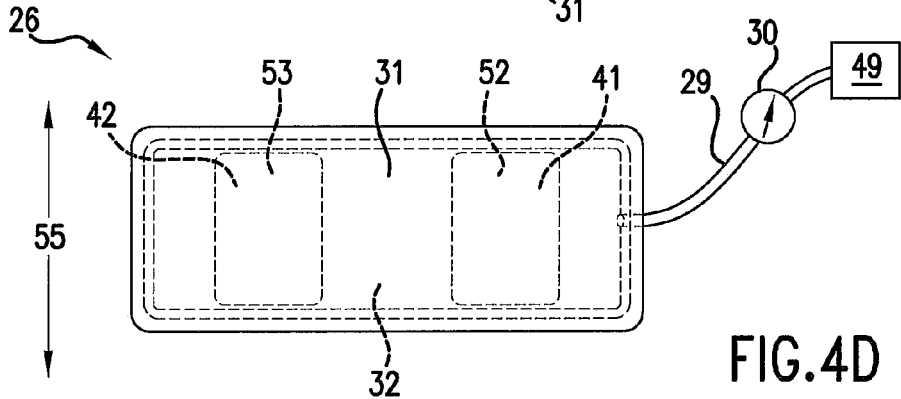
FIG. 4D is a front view of the device of FIG. 4A in an actuated state.

A pressure source 49 is included and is placed into fluid communication with the first longitudinal carotid expandable member 27 by way of pressure tubing 29 that extends through a port of member 27. A manometer 30 may be included in the device 26 at some point between the member 27 and the pressure source 49 in order to monitor and measure pressure in the system. FIGS. 3C and 3D illustrate the device 26 once the pressure source 49 is activated in order to cause the device 26 to be pressurized. The pressure source 49 may be a pump that injects air, gas or liquid, such as water, through the pressure tubing 29. Injection of air or otherwise increasing the pressure causes the first longitudinal carotid expandable member 27 to expand. Due to fluid communication through the connecting tube 54, the second longitudinal carotid expandable member 46 will likewise expand and the two members 27 and 46 may expand at the same rate to the same size. Expansion may be in the radial direction 57 such that the expandable members 27 and 46 expand towards the central axis 56 and away from the central axis 56. In some exemplary embodiments, the members 27 and 46 may expand in the radial direction 57 towards the central axis 56 but not in the radial direction 57 away from the central axis 56. This arrangement may be accomplished by making portions of the expandable members 27 and 46, for example the portions facing away from the central axis 56 in the radial direction 57, such that they cannot expand while the portion facing towards the central axis 56 are in fact expandable. The expandable members 27 and 46 may be inflated to a pressure level that is above the level of the patient's arterial pressure to achieve temporary interruption of the carotid blood flow. Both the left and right carotid arteries 16 can be compressed at the same time.

Additionally or alternatively, the insertion pockets 41 and 42 could have portions that are made of different materials so that the parts facing the central axis 56 in the radial direction 57 are expandable while the parts facing away from the central axis 56 in the radial direction 57 are not expandable. The expandable members 27 and 46 are elongated in the vertical direction 55, which is the same direction as the central axis 56. However, it may be the case that upon expansion of the expandable members 27 and 46 from the unactuated to the actuated states the expandable members 27 and 46 do not expand in the vertical direction 55.

The exemplary embodiment of the device 26 in FIGS. 3A-3D does not include a transverse carotid expandable member 32 but instead includes only two expandable members 46. The device 26 may be placed onto the patient so that the first longitudinal carotid expandable member 27 overlays the carotid artery 16 such that the carotid artery 16 is located between the central axis 56 and the member 27 in the radial direction 57. The second longitudinal carotid expandable member 46 may be laid on top of the other carotid artery 16 such that the second carotid artery 16 is likewise between the member 46 and the central axis 56 in the radial direction 57.

Expansion forces of the expandable members 27 and 46 may be imparted onto the carotid arteries 16 so that they are compressed thus forming the areas of compression 23 as previously discussed. The pressure in the expandable members 27 and 46 may be set so as to exceed the patient's systemic pressure to achieve adequate compression of the carotid arteries 16 to have a transient "no-flow" effect. In some arrangements the pressure of the members 27, 32 and/or 46 may exceed the patient's systemic pressure by 10-20 mm Hg, or up to 30 mm Hg or higher in accordance with certain exemplary embodiments. In some embodiments the expandable members 27, 32 and 46 are inflated to a pressure exceeding the patient's systemic pressure by at least 10 mm Hg. Once the "emboligenic" part of the procedure is completed, the pressure in members 27 and 46 may be released in order to establish carotid arterial flow.

Another exemplary embodiment of the device 26 is illustrated in FIGS. 4A-4D. The device 26 in this exemplary embodiment also functions to compress the carotid arteries 16 to create the areas of compression 23. The device 26 includes a first insertion pocket 41 and a second insertion pocket 42 but lacks first and second longitudinal carotid expandable members 27 and 46. Instead a first compression member 52 is located within the first insertion pocket 41, and a second compression member 53 is located within the second insertion pocket 42. The compression members 52 and 53 are not expandable but may be made of a material, such as foam, that can be compressed and then can subsequently expand back into its original shape. The compression members 52 and 53 may alternatively be made of a material that does not exhibit any give upon the application of forces thereto that would be encountered in a procedure of the type described herein. The compression members 52 and 53 may be elongated in the vertical direction 55 and may have a convex shape that faces the central axis 56. The shape of the compression members 52 and 53 at their surfaces that face away from the central axis 56 in the radial direction 57 may be different than those that face towards the central axis 56.

The device 26 may include a transverse carotid compression section 31 that is located outward from the compression members 52 and 53 in the radial direction 57 from the central axis 56. A transverse carotid expandable member 32 may be held by the section 31 and can have an arc length about the central axis 56 that extends beyond both of the compression members 52 and 53. The transverse carotid expandable member 32 has a height in the vertical direction 55 that is the same as, larger or smaller than the height of the compression members 52 and 53 in the vertical direction 55. The member 32 is made of a material that will hold air, gas or liquid such that it can be expanded upon the application of fluid thereto. The member 32 has a single port that is in fluid communication with the pressure tubing 29. Application of pressure to the member 32 will cause the member 32 to expand as shown for example in FIGS. 4C and 4D. In other embodiments, the compression members 52 and 53 can be removed and not present so that only the expandable member 32 is present to compress the carotid arteries 16.

The transverse carotid compression section 31 can be arranged so that all of it is expandable or so that only a portion of it expands as the member 32 expands. Boundary lines 50 and 51 may demarcate areas of the transverse carotid compression section 31 that can expand from those that cannot expand. For example, the portion of section 31 radially outward from the boundary lines 50 and 51 may not be capable of expansion while the portions of section 31 radially inward from boundary lines 50 and 51 are capable of stretching and thus expanding or contracting. This arrangement may cause expansion only, or primarily, in the radially inward direction upon expansion of the expandable member 32. In other embodiments, the section 31 is made of the same material and exhibits expansibility such that it generally expands in all directions equally. The expandable member 32 may be arranged so that it does not lengthen in the vertical direction 55 upon expansion, or in some arrangements only minimally expands in the vertical direction 55 when actuated.

Placement of the device 26 onto the patient may result in the first compression member 52 overlaying the carotid artery 16 so that the carotid artery 16 is between compression member 52 and the central axis 56 in the radial direction 57. The second compression member 52 will be arranged so that it overlays the second carotid artery 16 causing it to be between the second compression member 52 and the central axis 56 in the radial direction 57. The expandable members 27, 32 and 46 may be located at the neck of the patient such that they are secured to the neck or otherwise proximate the neck. The expandable members 27, 32 and 46 need not be in direct contact with the neck of the patient but only located near the neck of the patient. Application of pressure via the pressure source 49 causes the transverse carotid expandable member 32 to expand in the radial direction 57. This inward radial expansion causes the compression members 52 and 53 to move inwards and be urged against the carotid arteries 16. The positioning and configuration of the members 52 and 53 function to impart compressive forces onto the carotid arteries 16 when the device 26 is pressurized thus resulting in the creation of the areas of compression 23. The other components of the device 26 may be made as those previously described and a repeat of this information is not necessary.

Although described as lacking first and second longitudinal carotid expandable members 27 and 46, an alternative arrangement may be made in which these members 27 and 46 are present. In such an arrangement, the expandable members 27 and 46 may expand in order to press the compression members 52 and 53 towards the carotid arteries 16.

Figure 5:
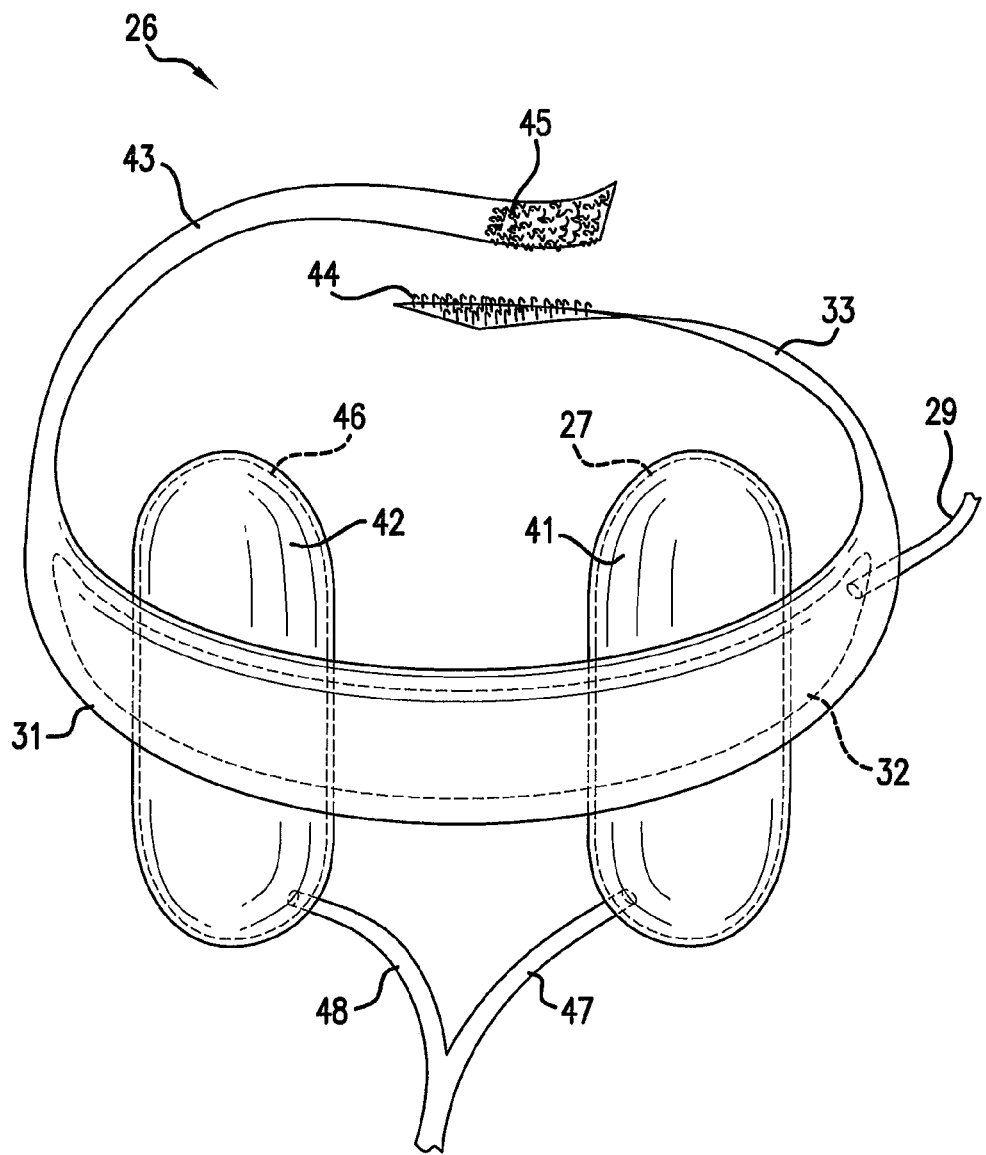
FIG. 5 is a perspective view of a device with a transverse carotid expandable member and two longitudinal carotid expandable members in accordance with another exemplary embodiment.

An alternative exemplary embodiment of the device 26 is illustrated with reference to FIG. 5 in which both a pair of longitudinal carotid expandable members 27 and 46 are present along with a transverse carotid expandable member 32. A pair of compression members 52 and 53 may be missing from this embodiment, or they may be present in certain arrangements. This exemplary embodiment includes additional pressure tube lines 47 and 48 that are separate from pressure tubing 29 that actuates the transverse carotid expandable member 32. Pressure tube lines 47 and 48 provide pressure to the first and second longitudinal carotid expandable members 27 and 46 so that these members 27 and 46 can be expanded at different rates, amounts, and/or times than expandable member 32. This flexibility provides selective pressure adjustments between the transverse carotid expandable member 32 and the pair of longitudinal carotid expandable members 27 and 46. This feature will provide an option to decrease or completely eliminate the degree of circumferential neck compression when selective inflation of the two longitudinal carotid expandable members 27 and 46 is adequate. Conversely, if inflation of members 27 and 46 does not lead to sufficient reduction of the carotid flow, an additional inflation of the expandable member 32 would allow one to achieve the desired effect by combining the effect of pressure created in all of the members 27, 46 and 32.

The preferred method of carotid artery 16 compression in this case will be an initial inflation of members 27 and 46, followed by inflation of member 32 when necessary. The degree of interruption of the carotid flow in this and other embodiments can be checked by the data of carotid Doppler, trans-cranial Doppler, pulsation of the temporal arteries and other techniques of assessment of the carotid and cerebral perfusion. The other components of the device 26 are the same as those previously disclosed with respect to other embodiments and a repeat of this information is not necessary.

An alternative exemplary embodiment of the device 26 is disclosed with reference to FIGS. 6A-6D. The embodiment disclosed is similar to that previously disclosed with respect to FIG. 5 and a repeat of the features and functionality that are similar between the two need not be repeated. The pressurization of the members 27, 32 and 46 are different in that the second pressure tube 47 feeds into the first longitudinal carotid expandable member 27, and in that the third pressure tube 48 supplies the second longitudinal carotid expandable member 46 to allow the members 27 and 46 to be pressurized independently from one another. In this regard, one can apply more or less pressure to member 27 than member 46 so that compression of the carotid arteries 16 can be more precisely controlled. The transverse carotid expandable member 32 is supplied by pressure tubing 29 and is independent from the expansion of members 27 and 46 such that it can be pressurized to a greater or lesser extent than members 27 and 46. The manometer 30 may be capable of measuring pressures in all of the lines 29, 47 and 48 so that their individual pressures can be monitored. In use, one may adjust the pressures in members 27 and 46 first, then subsequently if needed one may apply pressure into member 32 to cause its expansion so that adequate compression of the carotid arteries 16 is realized.

The ports for the pressure lines 47 and 48 may be located at the bottom of the expandable members 27 and 46 in the vertical direction 55. However, the ports for pressure lines 47 and 48 need not be in the disclosed locations in accordance with other exemplary embodiments and may be above the transverse carotid compression section 31 or at the same location as the section 31 in the vertical direction 55 in other exemplary embodiments. The insertion pockets 41 and 42 although described as being sealed may have an opening into which the expandable members 27 and 46 may be removed and into which first and/or second compression members 52 and 53 may be inserted so that the device 26 can function with the compression members 52 and 53 and transverse carotid expandable member 32 as previously discussed.

Figure 6A:
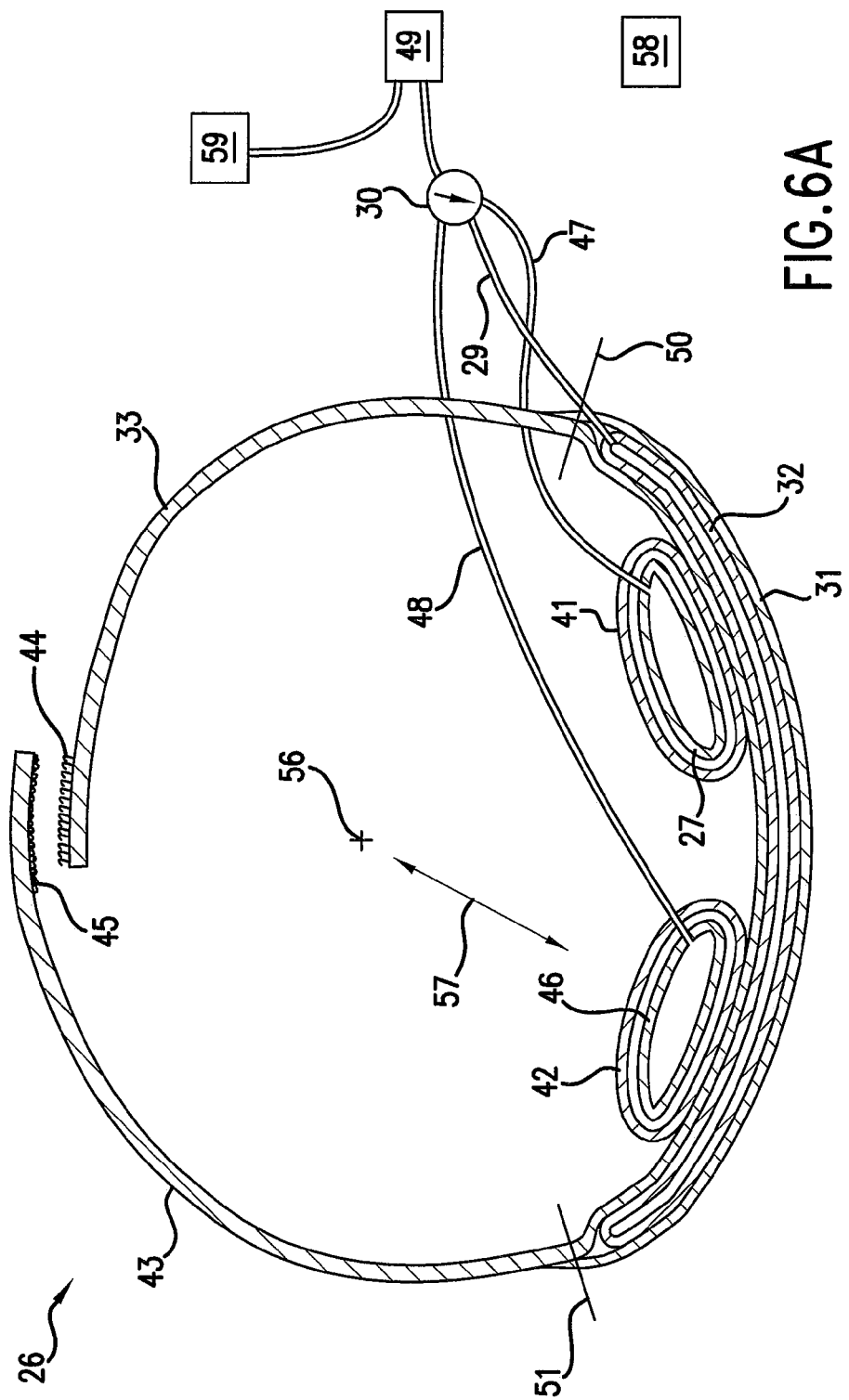
FIG. 6A is a cross-sectional view of the device of FIG. 5 in an unactuated state.
Figure 6B:
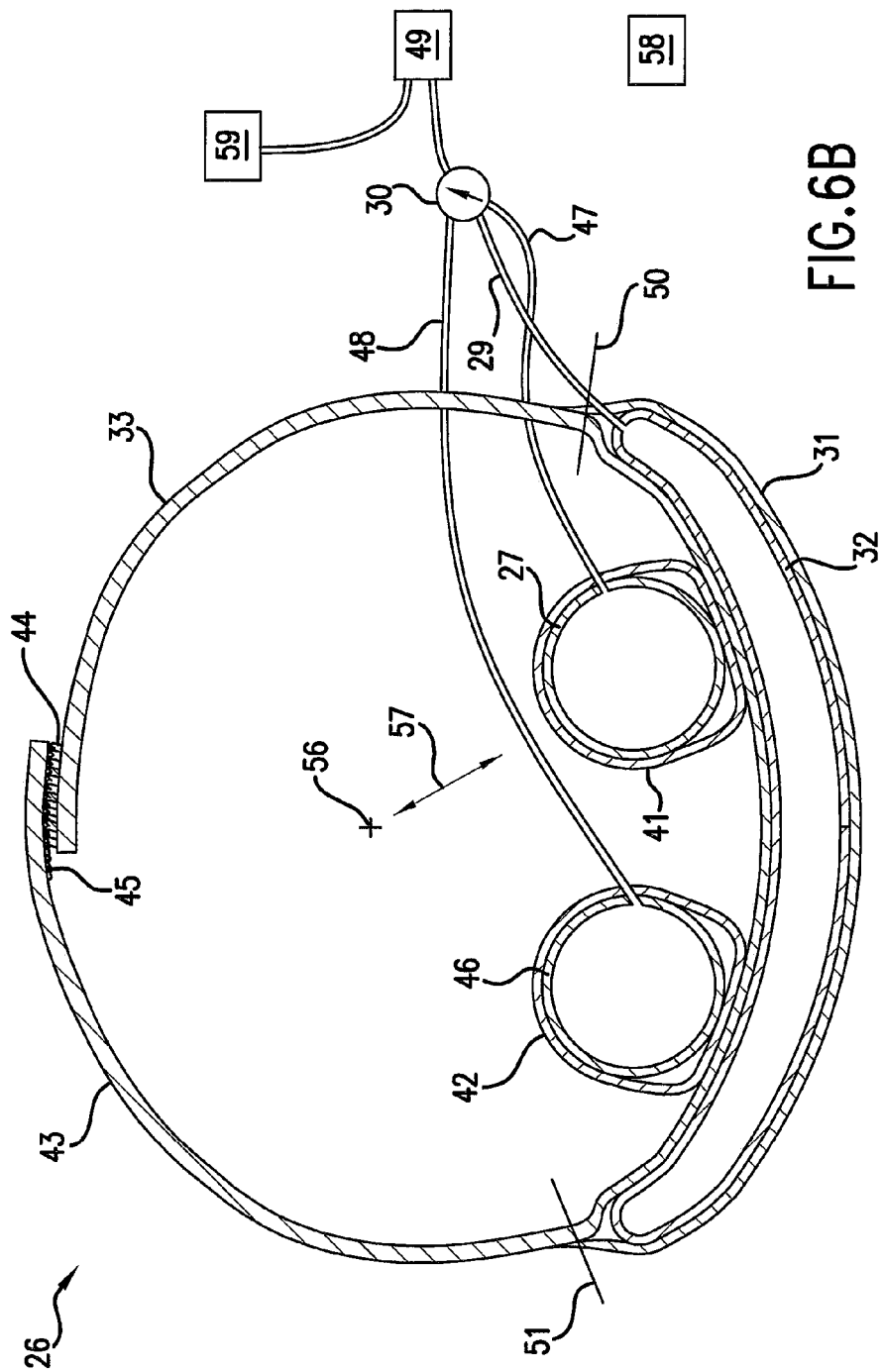
FIG. 6B is a cross-sectional view of the device of FIG. 5 in an actuated state.
Figure 6C:
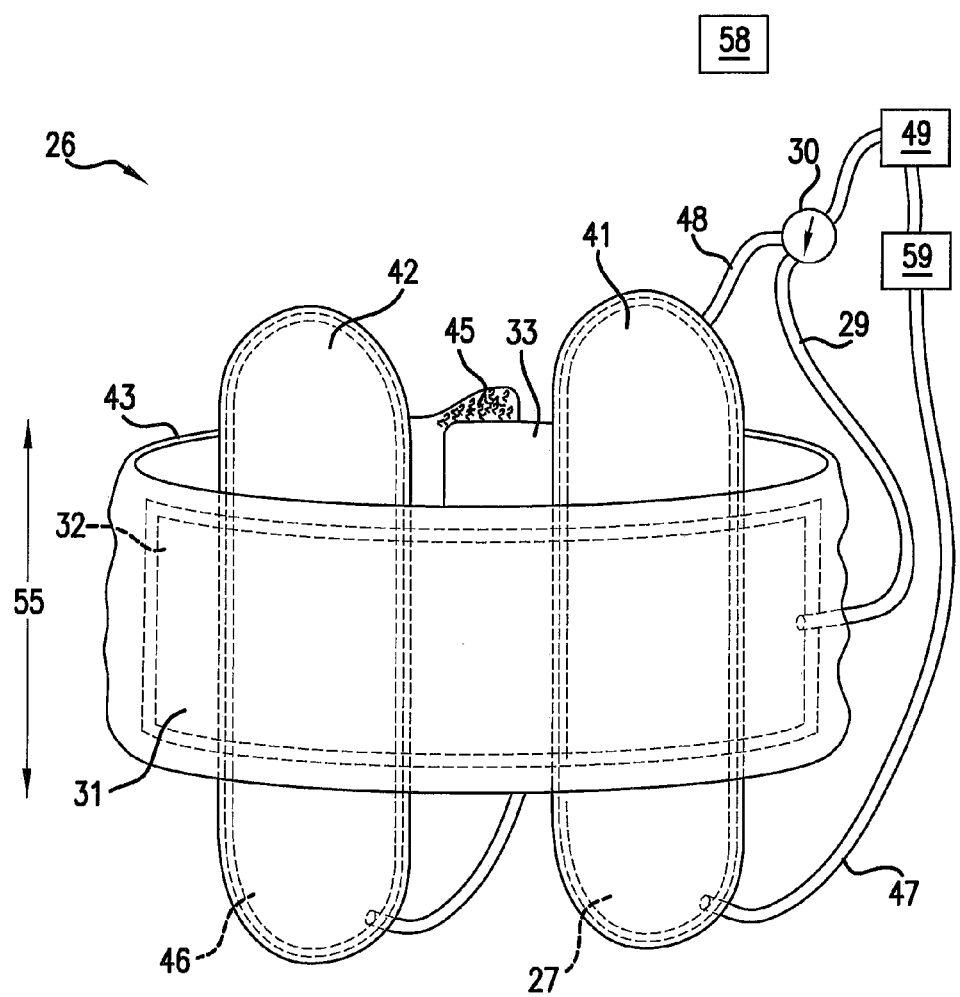
FIG. 6C is a front view of the device of FIG. 5 in an unactuated state.
Figure 6D:
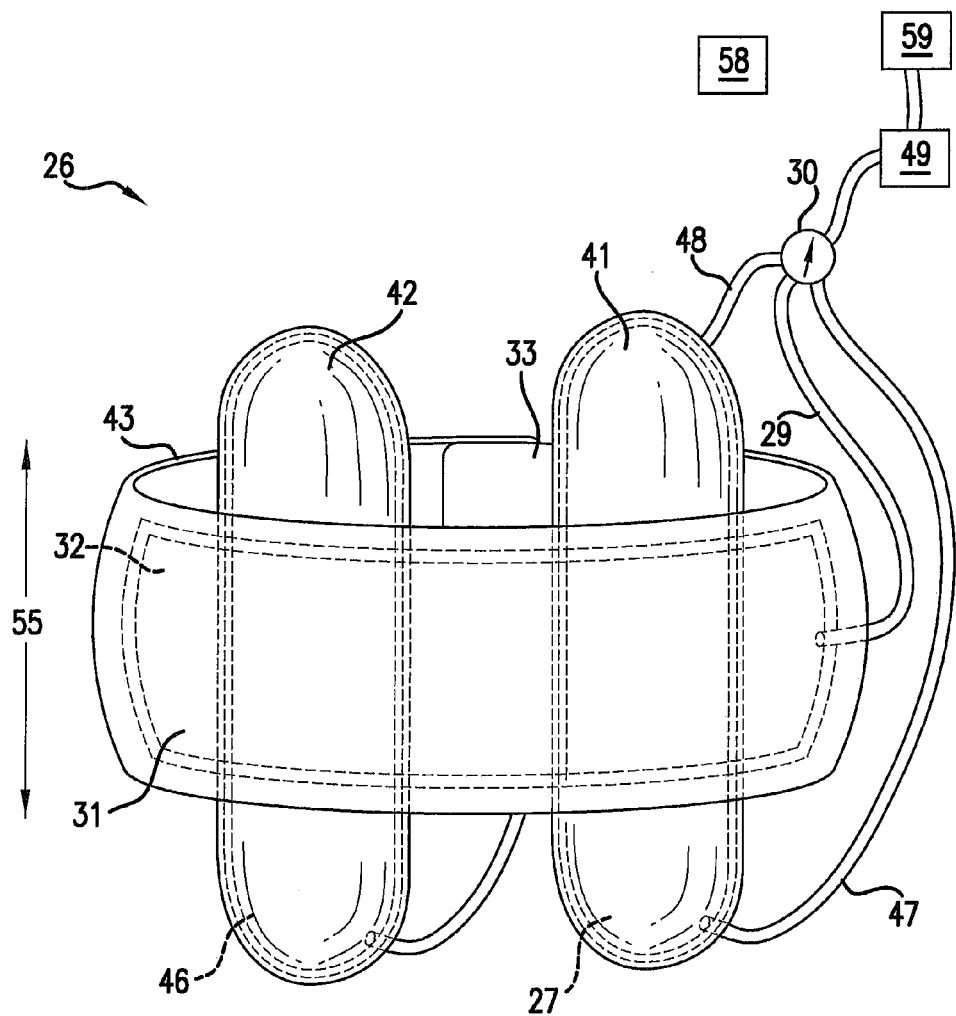
FIG. 6D is a front view of the device of FIG. 5 in an actuated state.

The arrangement of the device 26 in FIGS. 6A-6D thus includes a pair of longitudinal carotid expandable members 27 and 46 along with a transverse carotid expandable member 32. With reference to FIG. 6B, the boundary lines 50 and 51 may be located at the boundaries of the straps 33 and 43 and the transverse carotid compression section 31. The lengths of the members 27 and 46 in the vertical direction 55 are each longer than the length of the member 32 in the vertical direction 55, and the arc length of the member 32 is larger than the arc lengths of the members 27 and 46 combined. The transverse carotid expandable member 32 may have an arc length that extends up to 65% of the circumferential distance about the central axis 56. In this regard, the member 32 may have an arc length that is up to 234 degrees about central axis 56. The circumferential distance about the central axis 56 may also be the circumferential distance about the neck of the patient when the device 26 is worn by a patient and thus these two terms can be interchangeable when discussing the arc length of the member 32. In other exemplary embodiments, the arc length of the member 32 may be from 50-65% (180 degrees-234 degrees) about the circumference of the neck of the patient, from 25%-50% (90 degrees-180 degrees) about the circumference of the neck of the patient, or from 15%-25% (54 degrees-90 degrees) about the circumference of the neck of the patient. In yet other exemplary embodiments, the member 32 may extend 360 degrees completely about the central axis 56/neck of the patient.

The members 27 and 46 are closer to the central axis 56 in the radial direction 57 than the member 32 is to the central axis 56. Comparison of FIGS. 6C and 6D demonstrate that the lengths of the members 27, 32 and 46 do not increase in the vertical direction 55, or in the arc length direction, upon moving from the unactuated orientation to the actuated orientation or only slightly expand in these directions upon actuation. The majority of the expansion may be in the radial direction 57 either towards the central axis 56 or away from the central axis 56 or a combination of the two. In other arrangements, however, expansion of the members 27, 32 and 46 may result in equal expansion in all directions. As previously stated, various components of the device 26 in FIGS. 6A-6D may be arranged and function in a manner similar to those as previously discussed and a repeat of this information is not necessary.

Figure 7A:
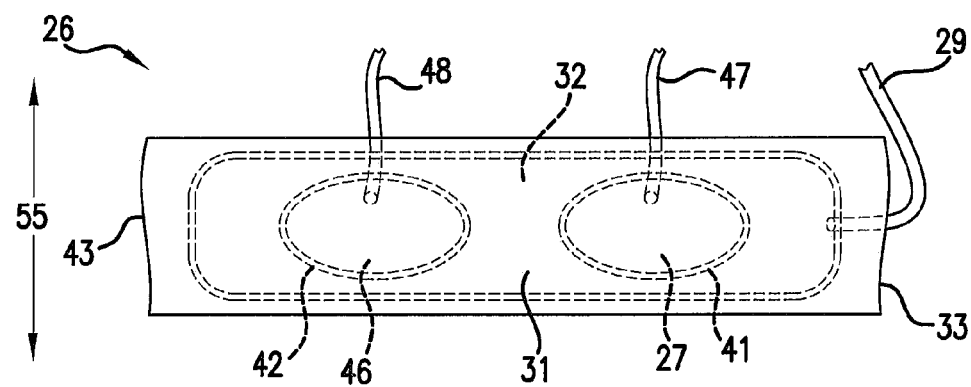
FIG. 7A is a front view of a device provided for patients with short and thick necks in accordance with another exemplary embodiment.
Figure 7B:
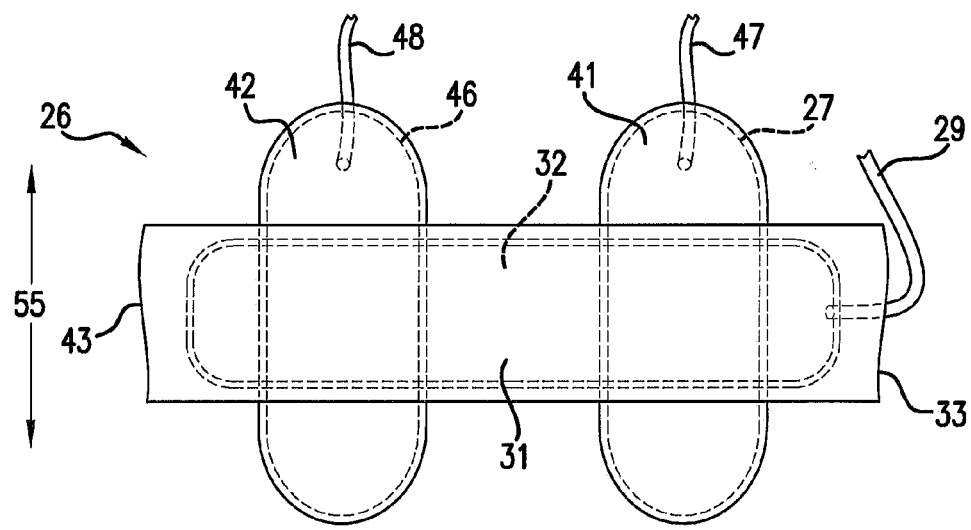
FIG. 7B is a front view of a device provided for patients with long and thin necks in accordance with yet another exemplary embodiment.

FIGS. 7A and 7B disclose modifications of the geometry of the members 27 and 46 with respect to the geometry of the transverse carotid expandable member 32 which is the same in both FIGS. 7A and 7B. The different geometries for members 27 and 46 may be due to variations of neck anatomy in each patient. In patients with a short and large neck the embodiment in FIG. 7A may be employed that has longitudinal carotid expandable members 27 and 46 that are bigger and more round to achieve more efficient carotid compression. The length of each one of the members 27 and 46 in the vertical direction 55 may be less than the length of the member 32 in the vertical direction 55 both when all of the members 27, 32 and 46 are unexpanded, and when all of the members 27, 32 and 46 are expanded. In patients with a long and thin neck the preferred embodiment comprises the members 27 and 46, as shown in FIG. 7B, that are more oval and narrow for the same reason of more efficient carotid compression to account for the differences in neck geometries of patients. The lengths of each of the members 27 and 46 in the vertical direction 55 is longer than the length of the member 32 in the vertical direction 55 both when all of the components 27, 32 and 46 are unactuated and when they are all actuated.

Figure 8B:
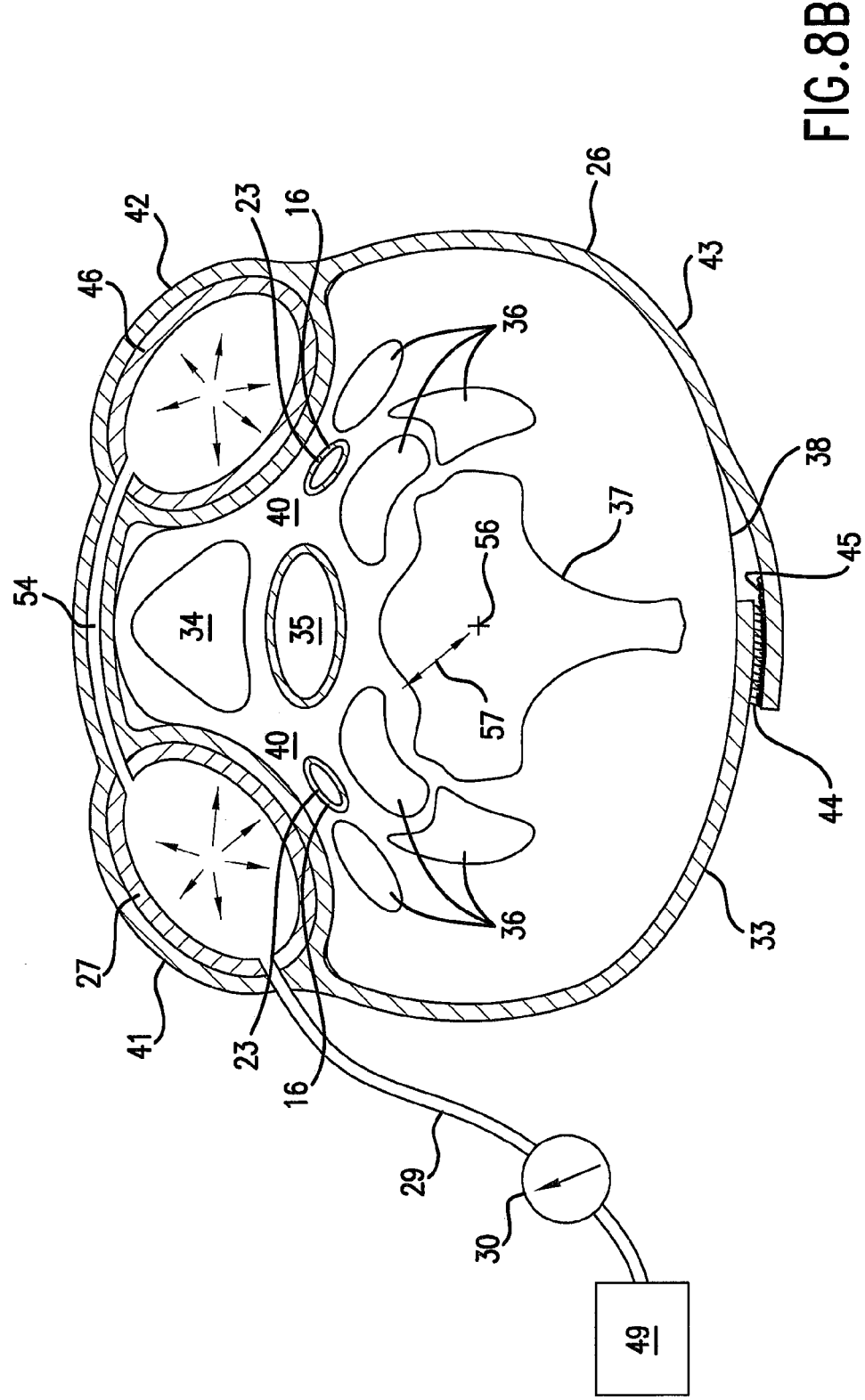
FIG. 8B is a cross-sectional view of a neck of a patient and a device attached thereto in an actuated state.

FIGS. 8A and 8B demonstrate the method of use and the effect of inflation of the device 26 resulting in external compression of both carotid arteries 16, leading to transient interruption of carotid flow. These two figures demonstrate the anatomic relationship of the device 26 to both carotid arteries 16 and surrounding structures 34, 35, 36, 37 and 40. The carotid arteries 16 are bordered by neck muscles 36, esophagus 35, trachea 34 and fat tissues 40. These structures provide a protective cushion, minimizing the risk of carotid injury during external compression. In fact, an external compression of carotid arteries 16 in this setting would lead to significantly lower risk of injury to carotid intima than intravascular carotid occlusion with the balloon or umbrella devices used for cerebral protection in patients undergoing carotid stenting. The longitudinal carotid expandable members 27, 46 are positioned along the course of both carotid arteries 16 on the neck.

The exemplary embodiment of the device 26 may be any one of those previously disclosed that lacks a transverse carotid expandable member 32. However, it is to be understood that this is just one example and that other devices 26 that include member 32 can function in a similar manner to the device 26 disclosed in FIGS. 8A and 8B. As shown in FIG. 8A, one of the longitudinal carotid expandable members 27 is placed along the course of one of the carotid arteries 16, and the other expandable member 46 is placed along the course of the other carotid artery 16. The lumen of both carotid arteries is compressed between the inflated bladders 27 and 46 anteriorly (outward in the radial direction 57) and the cervical spine 37 posteriorly (inward in the radial direction 57). Actuation of the members 27 and 46 cause the members to move radially inward and compress fat tissue 40 that is immediately adjacent the device 26. The expandable members 27 and 46 are shown moving in the radial direction 57 inward of portions of the trachea 34 and neck muscles 36 so that portions of the expandable members 27 and 46 are closer to the central axis 56 in the radial direction 57 than portions of the trachea 34 and neck muscles 36. Full expansion of the expandable members 27 and 46 may result in inward radial movement so that they are not radially closer to the axis 56 than any portion of the esophagus 35. However, other embodiments are possible in which at least some portion of the expandable members 27 and 46 are closer to the central axis 56 than a portion of the esophagus 35.

The soft tissues such as the fat tissues 40, neck muscles 36, esophagus 35 and trachea 34 around carotid arteries 16 provide a smooth cushion assuring adequate protection against carotid trauma. Expansion of the members 27 and 46 causes the areas of compression 23 to restrict blood flow through the carotid arteries 16 which leads to transient interruption of carotid flow. The trachea 34 and esophagus 35 are not closed or restricted upon actuation of the expandable members 27 and 46 due to the placement and specific configuration of the expandable members 27 and 46. However, in some arrangements some degree of restriction of the trachea 34 and/or esophagus 35 may occur when the expandable members 27 and 46 are expanded. It may be advisable, however, to obtain carotid Duplex scan in all patients planned for this procedure to rule out significant atherosclerotic disease of these vessels 16. If the patient is found to have severe carotid disease, the risk of dislodging the carotid plaque due to carotid compression should be weighed against the risk of stroke associated with the main cardiovascular intervention.

The divergence of potential cerebral emboli 17, 18 and prevention of stroke can be achieved by a noninvasive safe method that involves external compression of the carotid arteries 16. The method and device 26 disclosed do not require puncture of the skin or arteries and do not necessitate the use of endovascular devices. The device 26 and disclosed method allow for the divergence of emboli 17 and 18 of all sizes, including those microscopic particles that are too small to be trapped with the known intravascular filters.

Various types of mechanisms capable of compressing the carotid arteries 16 can be included in the device 26 in addition to or alternatively to those previously discussed. For example, the device 26 can be supplied with different carotid compression mechanisms, including different forms of longitudinal bladders, cuffs, compression pads or inserts with the same effect of carotid compression to the point of transient interruption of carotid flow. The fluid provided to pressurize the expandable components of the device 26 from the pressure source 49 may be a liquid substance in some embodiments. Fluid that is a liquid may be used in the device 26 to effect pressurization and more uniform constriction of the carotid arteries 16 than gas or air fluid because liquid is more non-compressible at the operating range of pressures. Liquid fluid in the members 27, 32 and 46 may more directly transmit pressure to the carotid area than gas or air fluid.

Further, although shown as employing a single pressure source 49, it is to be understood that multiple pressure sources 49 may be used. For instance, the transverse carotid expandable member 32 may be pressurized by a first pressure source 49 such as a pump, while a second source of pressure 49 is included in the device 26 to provide pressure to the two longitudinal carotid expandable members 27 and 46.

A monitoring system 58 may be included with the device 26 to assure a safe, adequate, easily manageable and controllable compression of carotid vessels 16. The monitoring system 58 may comprise Doppler ultrasound, Doppler probe, oscillotonometry, electroencephalography, transcranial Doppler, cerebral oximetry and/or other techniques. The device 26 may be actuated to such a degree that the two areas of compression 23 formed completely stop the flow of blood into the distal carotid artery 22, or to an extent that partial flow of blood passes through the areas of compression 23 and into the distal carotid artery 22 and cerebral circulation.

The device 26 provided is a noninvasive and precise apparatus with an option of assessing a degree and an effectiveness of an interruption of the carotid flow by the optional inclusion of a monitoring system 58. The device 26 assures a uniform and reproducible interruption of the carotid flow bilaterally minimizing the risk of trauma to the carotid artery wall and subsequent cerebral emboli 17. An alarm system 59 can be included in the device 26 that is triggered by excessive or lengthy compression of the carotid arteries 16. The alarm system 59 may be a part of the monitoring system 58 or may be a different component that is not part of the monitoring system 58. The alarm system 59 may thus measure the time of compression, and the magnitude of compression. Constant monitoring of carotid 16, systemic arterial and device 26 pressures with pressure in the device 26 exceeding only slightly the pressure in the arterial system may be conducted to ensure safe operation and use of the disclosed device 26. The device 26 provides a noninvasive compression apparatus that does not require the insertion of intravascular devices.

Figure 9:
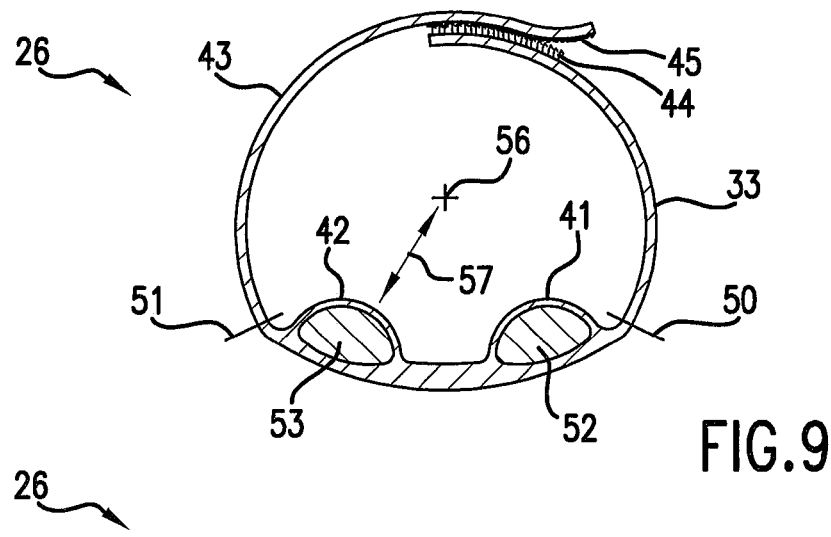
FIG. 9 is a cross-sectional view of a device in accordance with another exemplary embodiment.

With reference now to FIG. 9, an alternative exemplary embodiment of the device 26 is illustrated. Here, the device 26 lacks an expandable member 27, 32, or 46 and includes a compression member 52. The particular arrangement of FIG. 9 also includes a second compression member 53. The compression members 52, 53 are located within and held by first and second insertion pockets 41 and 42. The compression members 52 and 53 may be as previously described and a repeat of this information is not necessary. The compression members 52, 53 may be referred to as compression members because they function to compress the carotid arteries 16. The compression members 52, 53 may themselves be compressible such that they can be deformed when force is applied thereto to be compressed and hence smaller. When the force is removed the compression members 52, 53 can spring back to their non-compressed state. However, in some arrangements the compression members 52, 53 are not compressible themselves at all and maintain the same size and shape when force is applied. The compression members 52, 53 still function to compress the carotid arteries 16 even when they themselves are not compressible. The compression members 52, 53 function without being expanded by the pressure source 49. The device 26 of FIG. 9 lacks a pressure source 49 and no components of the device 26 are expandable.

A strap 33 extends from the boundary line 50 and has hooks 44 disposed thereon. Strap 43 extends from boundary line 51 and has loops 45 located on one surface thereof. The straps 33, 43 extend circumferentially around the central axis 56 and may surround the central axis 56 up to 240 degrees in some exemplary embodiments. The straps 33, 43 are adjustable in that they can be unattached from one another and then reengaged such that the points of contact between the hooks 44 and the loops 45 are changed. This change causes the relative size of the device 26 in the radial direction 57 to either increase to relive pressure on the neck of the patient, or decrease to increase the amount of pressure on the neck of the patient so that the compression members 52 and 53 apply greater pressure to the carotid arteries 16.

Although shown and described as a pair of straps 33, 43 it is to be understood that as used herein the term "strap" is broad enough to include a pair of straps, a single strap, or any other tightening mechanism. If a single strap is present it will extend from boundary line 50 to boundary line 51 and can be adjustable to increase pressure supplied by the device 26 to the neck of the patient, or non-adjustable such that it may function to hold the device 26 to the neck of the patient while some other mechanism functions to apply pressure to the compression members 52 and 53.

Figure 10A:
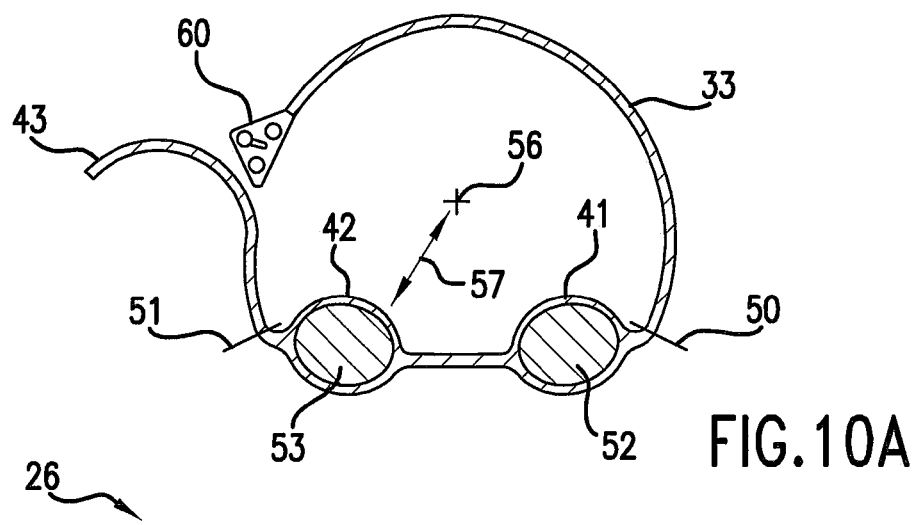
FIG. 10A is a cross-sectional view of a device in an untightened state in accordance with another exemplary embodiment.
Figure 10B:
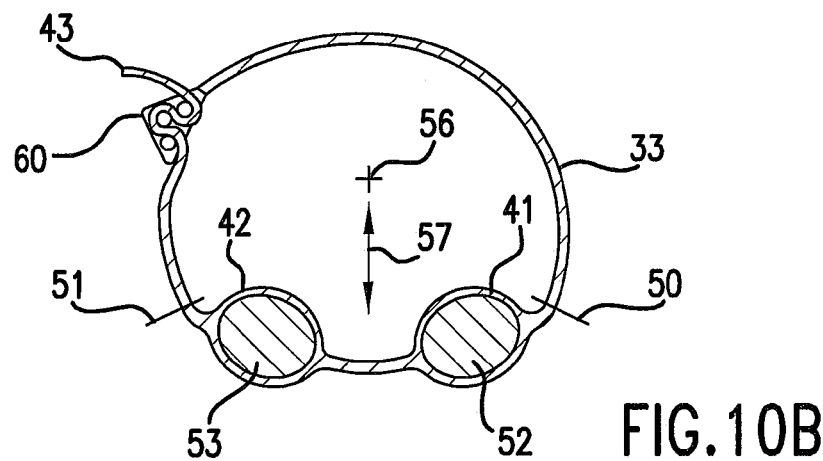
FIG. 10B is a cross-sectional view of the device of FIG. 10A in a tightened state.

Another exemplary embodiment of the device 26 is shown in FIGS. 10A and 10B. The device 26 includes a pair of compression members 52, 53 that are held by pockets 41 and 42. The compression members 52, 53 may apply pressure to the carotid arteries 16 and in this regard need to directly contact the skin of the neck of the patient. Instead, the insertion pockets 41 and 42 directly contact the skin of the neck of the patient, and the compression members 52, 53 apply pressure to the carotid arteries 16 by exerting force through the insertion pockets 41, 42 and into the neck of the patient. The embodiment in FIGS. 10A and 10B lacks a source of pressure and the device 26 does not have an expandable member.

Strap 33 extends from boundary line 50 of the device 26 and is longer than strap 43 that extends from boundary line 51. A lock and adjustment clip 60 is attached to the end of strap 33 and this attachment may be a permanent attachment. Strap 43 is not attached to the lock and adjustment clip 60 in FIG. 10A. The health care provider may place the device 26 around the neck of the patient so that the compression members 52, 53 overlay the carotid arteries 16 of the patient. The strap 43 could be moved through the lock and adjustment clip 60 and secured thereto so that the strap 43 is attached to the strap 33 to cause the device to be held onto the neck of the patient. However, the tightening of the strap 43 relative to strap 33 may be loose such that the compression members 52, 53 do not apply pressure to the carotid arteries 16.

When compression of the carotid arteries 16 is desired, the health care provider may adjust the strap 43 relative to the lock and adjustment clip 60 as shown for instance in FIG. 10B. The health care provider can move a desired amount of the length of strap 43 through the lock and adjustment clip 60 and then lock the strap 43 to the lock and adjustment clip 60 so that it does not move relative thereto. This adjustment causes the size of the device 26 in the radial direction 57 to decrease, relative to the size in FIG. 10A, and forces the compression members 52, 53 against the carotid arteries 16 to compress the carotid arteries 16. The straps 33, 43 thus function to not only hold the device 26 onto the neck of the patient, but to also apply the pressure necessary for compressing the carotid arteries 16.

Other arrangements of the device 26 are possible. For example, the straps 33 and 43 can be located on the device 26 to hold the device 26 onto the patient but not to provide force that causes the compression members 52, 53 to be pressed against the carotid arteries 16. The device 26 may lack any members that are expandable, and thus may lack a pressure source 49. A belt or other mechanism can be wrapped around the compression members 52, 53 and may be tightened so that force from this tightening is transferred to the compression members 52, 53 so that they in turn will be urged against the carotid arteries 16 to close the carotid arteries 16.

A method for reducing or totally preventing cerebral emboli will now be discussed. A brief compression of carotid arteries 16 by way of a device 26 may be performed first to assure adequate position of the device leading to reduction or interruption of carotid flow or pulse as assessed by carotid Doppler, a pressure gauge, percutaneous cerebral oximetry or transcranial Doppler.

Once an adequate position of the device 26 is confirmed, the pressure in the carotid compression components (27, 32 and 46) is released and the apparatus 26 is ready for use. The device 26 is inflated to the pressure exceeding patient's systemic pressure just before proceeding with the emboligenic part of the procedure. Adequate compression of carotid arteries 16 will lead to physiological reduction of flow through vertebral arteries leading to further divergence of blood and emboli away from all cerebral vessels and toward more distal arteries, thus decreasing the risk of stroke.

The pressure in the device 26, and thus to the expandable components 27, 32 and 46 is released after the emboligenic procedure is completed after a full washout of potential emboli 20, 18 from the heart 11 and thoracic aorta 12. The expandable components 27, 32 and 46 are deflated approximately 30-90 seconds after the emobliogenic procedure is completed after a full washout of potential emboli 20, 18 from the heart 11 and thoracic aorta 12. The pressurization of the device 26 can be repeated any time and on multiple occasions when the emboligenic intervention is contemplated.

Should the physician or physician's assistant forget to release carotid compression timely, an alarm would go off and the pressure would be released spontaneously to avoid undue interruption of the cerebral flow. The alarm and deflation could be overridden by the physician when clinically indicated. The alarm may be sounded by the alarm system 59, and the deflation may be activated by the pressure source 49 and/or the alarm system 59 and/or the monitoring system 58.

The central axis 56 may be present even when the device 26 is not configured with straps 33, 43 to form a generally circular member when viewed from the top as for example in FIG. 6A. In some embodiments of the device 26, a circular member is not formed when viewed from the top by the straps 33, 43. For instance, the straps 33, 43 may be missing such that the section 31 is attached to sides of a bed or otherwise secured so that the device 26 is located at the neck of the patient. In such instances, the central axis 56 is still present. The central axis 56 may be located at a location within the neck of the patient, for examples shown with reference to FIGS. 8A and 8B. This location may be at the spinal column 37 of the patient, or may be at the center of the neck of the patient. It is to be understood that various embodiments of the device 26 exist in which the device 26 does not wrap completely around the neck of the patient but instead only wraps around a portion of the neck of the patient less than 360 degrees fully about the neck of the patient.

The device 26 may be provided so that no portion of the device 26 is inside of the patient and all of the device 26 is located outside of the patient. The method may be performed such that nothing is inserted inside of the patient to deflect the emboli 18. In this manner, the device 26 is not an invasive device as no portion is located within the carotid arteries 16 or under the skin or otherwise inside of the patient. The device 26 may be arranged so that it contacts the neck of the patient but not other parts of the patient such as the head of the patient, the arm of the patient, the leg of the patient, the chest of the patient, or the back of the patient. The device 26 may function to compress the carotid arteries 16 but not any other arteries of the patient. In this regard, the only arteries that are compressed by the device 26 are the carotid arteries 16.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A method of diverting emboli from cerebral circulation, comprising:
   placing a device at a neck of a patient, the device comprising members configured to compress carotid arteries of the patient, wherein each of the members comprises a foam or is nonporous, expandable, and capable of holding a fluid;
   positioning a first of the members at a first of the carotid arteries;
   positioning a second of the members at a second of the carotid arteries;
   compressing the first carotid artery by the first member and compressing the second carotid artery by the second member during a procedure on the patient, wherein the pressure applied by the first member and the second member exceeds a systemic pressure of the patient by at least 10 mm of Hg, wherein the procedure comprises a time period during which emboli released upstream from the first and second carotid arteries move towards the first and second carotid arteries and may move toward the patient's brain, and wherein the first member and the second member reduce blood flow in the carotid arteries, resulting in diversion of emboli away from the carotid arteries of the patient by flowing through a descending aorta of the patient instead of into the first and second carotid arteries; and
   releasing compression of the first and second carotid arteries.

2. The method of claim 1, further comprising positioning each of the first member and the second member between a trachea and neck muscles of the patient.

3. The method of claim 1, further comprising:
   applying pressure to the first member and the second member to cause each of the first member and the second member to expand from a non-expanded state to an expanded state, wherein in the expanded state the members apply the compression to the carotid arteries.

4. The method of claim 1, further comprising:
monitoring blood flow in the carotid arteries when compressing the first and second carotid arteries.

5. The method of claim 1, further comprising alarming when the first carotid artery and the second carotid artery have been compressed for a certain amount of time.

6. The method of claim 1, further comprising:
positioning a third member over the first and second members; and
applying pressure to the third member to expand the third member from a non-expanded configuration to an expanded configuration, thereby urging the first and second members in a direction toward a central axis of the neck of the patient.

7. The method of claim 6, wherein the third member comprises a partial or complete circumferential relation to the neck of the patient, and provides inward compression of the carotid arteries when expanded from the non-expanded configuration to the expanded configuration.

8. The method of claim 7, further comprising application of each of the first and second members to a respective side of the neck, wherein the first and second members are positioned between the patient's skin and the third member.

9. The method of claim 6, wherein at least one of the first and second members overlaps a course of one of the carotid arteries in a longitudinal direction, and wherein the third member overlaps a course of the least one of the carotid arteries in a transverse direction.

10. The method of claim 1, further comprising:
varying a degree of pressure in at least one of the first or the second member to regulate a degree of compression of at least one of the carotid arteries.

11. The method of claim 1, wherein the first member comprises a connection to a pressure source via a first tube, and the second member comprises a connection to the first member via a second tube, further comprising:
applying pressure from the pressure source;
wherein the first member receives the pressure via the first tube and expands from a non-expanded configuration to an expanded configuration, and the second member receives the pressure via the second tube and expands from a non-expanded configuration to an expanded configuration.

12. The method of claim 1, wherein the first member comprises a connection to a pressure source via a first tube, and the second member comprises a connection to the pressure source via a second tube, further comprising:
applying pressure from the pressure source;
wherein the first member receives the pressure via the first tube and expands from a non-expanded configuration to an expanded configuration, and the second member receives the pressure via the second tube and expands from a non-expanded configuration to an expanded configuration.

13. The method of claim 1, wherein the emboli comprise fragments of atherosclerotic plaque released during the time period.

14. The method of claim 1, wherein the procedure comprises at least one of an aortic valvuloplasty, an aortic valve implantation, a coronary intervention, a cardiac ablation, and an endovascular procedure.

15. The method of claim 1, wherein the first member and the second member each comprise a material that can be compressed and that can subsequently expand back into an original shape.

16. The method of claim 15, wherein the first member and the second member each comprise foam.

17. The method of claim 1, further comprising inserting the first member into a first insertion pocket of the device, and inserting the second member into a second insertion pocket of the device.

18. The method of claim 1, wherein the time period occurs during at least one of an aortic cross clamp manipulation, heart manipulation, heart valve manipulation, cardiac ablation manipulation, coronary artery manipulation, aorta manipulation.

19. The method of claim 18, wherein the compressing of the first and second carotid arteries occurs throughout the time period.

20. The method of claim 1, wherein the compressing of the first and second carotid arteries occurs throughout the time period.

21. The method of claim 1, wherein the compressing of the first and second carotid arteries begins prior to the time period and continues at least until the time period has ended.

22. The method of claim 21, further comprising compressing the first and second carotid arteries for a time from approximately 30-90 seconds after the time period has ended to achieve a washout of the emboli from the heart and the thoracic aorta.

23. The method of claim 1, wherein the emboli comprise air bubbles and thrombi.

24. The method of claim 1, wherein the compression of the first and second carotid arteries is released after the time period has ended.

25. The method of claim 1, wherein the emboli form as a consequence of the procedure.

26. A method of diverting emboli from cerebral circulation comprising:
placing a device at a neck of a patient, the device comprising first and second means for compressing respective first and second carotid arteries of the patient;
compressing the first carotid artery by the first means and compressing the second carotid artery by the second means during a procedure on the patient, wherein the pressure applied by the first and second means exceeds a systemic pressure of the patient by at least 10 mm of Hg, wherein the procedure comprises a time period during which emboli released upstream from the first and second carotid arteries move towards the first and second carotid arteries and may move toward the patient's brain, and wherein the first and the second means reduce blood flow in the carotid arteries, resulting in diversion of emboli away from the carotid arteries of the patient by flowing through a descending aorta of the patient instead of into the first and second carotid arteries; and
releasing compression of the first and second carotid arteries.

27. The method of claim 26, wherein the emboli form as a consequence of the procedure.

28. The method of claim 26, wherein the releasing compression starts after an amount of time has elapsed after the time period to achieve a washout of emboli released.

* * * * *